United States Patent
Atchaneeyasakul et al.

(10) Patent No.: US 11,291,463 B2
(45) Date of Patent: Apr. 5, 2022

(54) METHODS AND APPARATUS FOR RESTORING FLOW

(71) Applicant: Gravity Medical Technology, Inc., Carlsbad, CA (US)

(72) Inventors: Kunakorn Atchaneeyasakul, Pittsburgh, PA (US); Ashutosh P. Jadhav, Paradise Valley, AZ (US); Shashvat M. Desai, Phoenix, AZ (US)

(73) Assignee: Gravity Medical Technology, Inc., Carlsbad, CA (US)

( * ) Notice: Subject to any disclaimer, the term of this patent is extended or adjusted under 35 U.S.C. 154(b) by 0 days.

(21) Appl. No.: 17/336,791

(22) Filed: Jun. 2, 2021

(65) Prior Publication Data

US 2021/0378693 A1 Dec. 9, 2021

Related U.S. Application Data

(60) Provisional application No. 63/035,213, filed on Jun. 5, 2020.

(51) Int. Cl.
| | |
|---|---|
| *A61B 17/221* | (2006.01) |
| *A61B 90/00* | (2016.01) |
| *A61B 17/22* | (2006.01) |
| *A61B 17/00* | (2006.01) |

(52) U.S. Cl.
CPC ............ *A61B 17/221* (2013.01); *A61B 90/39* (2016.02); *A61B 2017/00336* (2013.01); *A61B 2017/22038* (2013.01); *A61B 2090/376* (2016.02); *A61B 2090/3966* (2016.02)

(58) Field of Classification Search
CPC .......... A61B 17/221; A61B 2017/2212; A61B 2017/2215; A61B 2017/22038; A61B 2017/22039; A61B 2017/00292; A61B 2017/003; A61B 2017/00336
See application file for complete search history.

(56) References Cited

U.S. PATENT DOCUMENTS

| | | | |
|---|---|---|---|
| 6,402,771 B1 * | 6/2002 | Palmer | A61B 17/221 606/114 |
| 6,575,997 B1 * | 6/2003 | Palmer | A61B 17/221 606/200 |
| 2011/0082493 A1 | 4/2011 | Samson et al. | |

(Continued)

FOREIGN PATENT DOCUMENTS

WO   2021247669   12/2021

OTHER PUBLICATIONS

"International Application Serial No. PCT US2021 035401, International Search Report dated Oct. 6, 2021", 2 pgs.

(Continued)

*Primary Examiner* — Wade Miles
(74) *Attorney, Agent, or Firm* — Schwegman Lundberg & Woessner, P.A.

(57) ABSTRACT

Methods and devices for removing an obstruction from a vessel include an elongate flexible shaft with an expandable capture cage coupled to the distal end of the elongate flexible shaft. The expandable capture cage has an expanded configuration and a collapsed configuration. The collapsed configuration is adapted to be delivered through the vessel and the expanded configuration is adapted to be expanded in the vessel to enmesh the obstruction.

37 Claims, 27 Drawing Sheets

(56) References Cited

U.S. PATENT DOCUMENTS

| | | | |
|---|---|---|---|
| 2011/0319917 A1* | 12/2011 | Ferrera | A61B 17/320725 606/159 |
| 2012/0083868 A1* | 4/2012 | Shrivastava | A61F 2/90 623/1.11 |
| 2014/0052162 A1* | 2/2014 | Cattaneo | A61M 25/0082 606/159 |
| 2014/0121672 A1 | 5/2014 | Folk | |
| 2014/0371779 A1* | 12/2014 | Vale | A61F 2/013 606/200 |
| 2015/0112376 A1 | 4/2015 | Molaei et al. | |
| 2016/0038174 A1 | 2/2016 | Bruzzi et al. | |
| 2016/0296245 A1 | 10/2016 | Yu | |
| 2017/0071614 A1* | 3/2017 | Vale | A61B 17/221 |
| 2017/0290599 A1* | 10/2017 | Youn | A61B 17/221 |
| 2018/0064454 A1* | 3/2018 | Losordo | A61B 17/221 |
| 2019/0336313 A1 | 11/2019 | Ferrera et al. | |
| 2019/0380726 A1* | 12/2019 | Grandfield | A61B 17/221 |
| 2021/0045761 A1* | 2/2021 | Choe | A61B 17/22 |

OTHER PUBLICATIONS

"International Application Serial No. PCT US2021 035401, Written Opinion dated Oct. 6, 2021", 10 pgs.

* cited by examiner

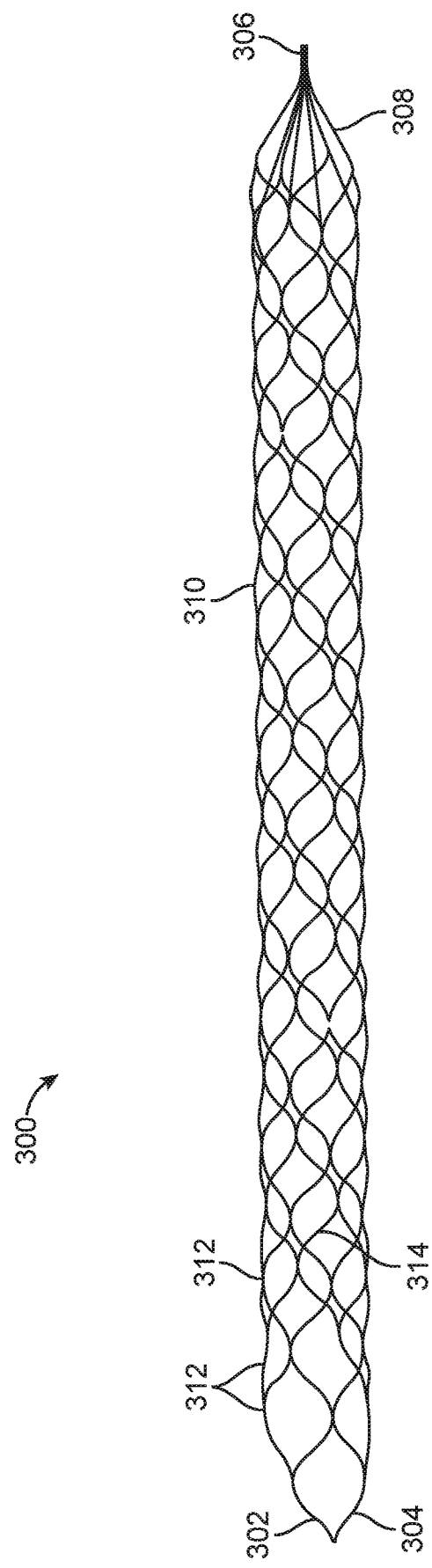

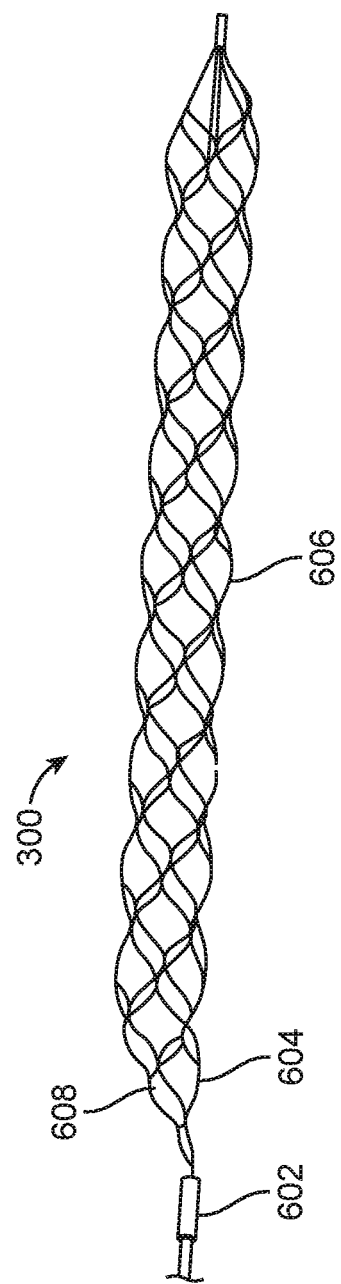

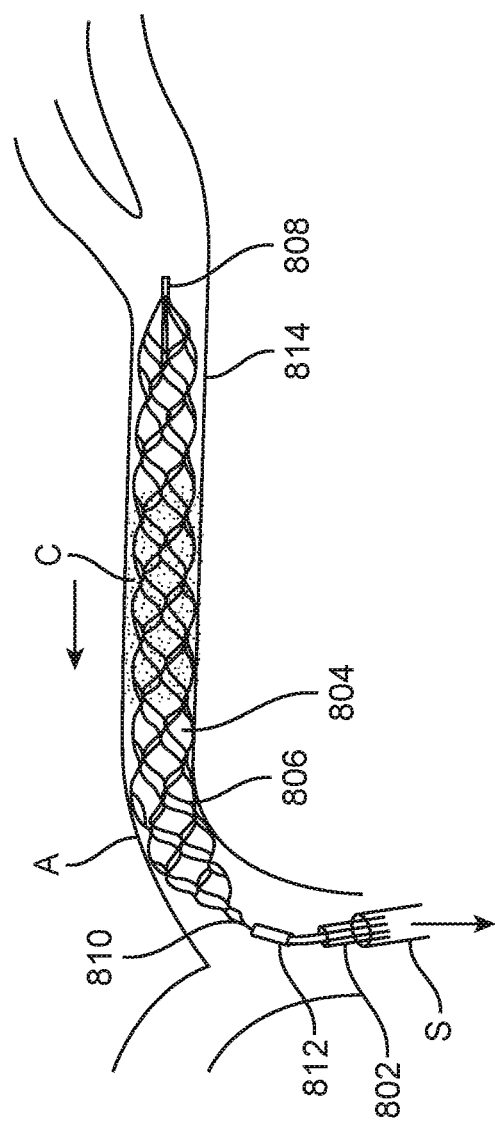

SECTION A-A

METHODS AND APPARATUS FOR RESTORING FLOW

CLAIM OF PRIORITY

The present application is a non-provisional of, and claims the benefit of U.S. Provisional Patent Application No. 63/035,213 (Attorney Docket No. 5543.001PRV) filed on Jun. 5, 2020; the entire contents of which are incorporated herein by reference.

BACKGROUND

Occlusion of a blood vessel is often caused by a clot and this may be referred to as a thromboembolic event, and can result in disorders such as stroke, pulmonary embolism, peripheral thrombosis, and the like. Thromboembolic events affect many people every year and may result in morbidity in patients throughout the world. Examples of morbidity include ischemia, loss of limb, angina pectoris, myocardial infarction, stroke, pulmonary embolism. In some cases, death may result as a result of a thromboembolic event.

Common existing techniques for treating thromboembolic events include embolectomy, surgery, the use of therapeutic agents such as streptokinase or urokinase or other thrombolytic agents, or thrombectomy devices.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 3A shows a side view of an example of an expandable capture cage that may be used with any device for removing obstructions.

FIG. 6A shows the expandable capture cage of FIG. 3A with optional varying strut dimensions.

FIG. 8A-8K illustrate an example of a method of removing a clot from a patient using any of the devices disclosed herein.

DETAILED DESCRIPTION

Occlusion of a blood vessel is often caused by a clot and this may be referred to as a thromboembolic event, and can result in disorders such as stroke, pulmonary embolism, peripheral thrombosis, and the like. Thromboembolic events affect many people every year and result in morbidity in patients throughout the world. Examples of morbidity include ischemia, loss of limb, angina pectoris, myocardial infarction, stroke, pulmonary embolism. In some cases death may result as a result of a thromboembolic event.

Commonly used techniques for treating thromboembolic events include embolectomy, surgery, the use of therapeutic agents such as streptokinase or urokinase or other thrombolytic agents, or thrombectomy devices, to name a few. These treatments provide varying degrees of clinical success and in some circumstances may not be optimal.

Therefore, there is a need to provide improved methods and devices for treating thromboembolic events that are safe, clinically effective, easy to use, and cost effective. It would be advantageous to provide a cost effective, minimally invasive device that can be accurately deployed at a target treatment region to retrieve clots. Such a device may also have a small profile to allow it to be delivered with a catheter through tortuous blood vessels to a treatment region far away from the vascular access point such as in the case of a neurovascular thrombus while minimizing disruption to blood flow. At least some of these objectives may be achieved by the examples disclosed herein which are generally related to medical devices and methods used during vascular intervention such as when treating thromboembolic disorders in the vascular system including clot removal from brain arteries in stroke patients.

Figure 1:
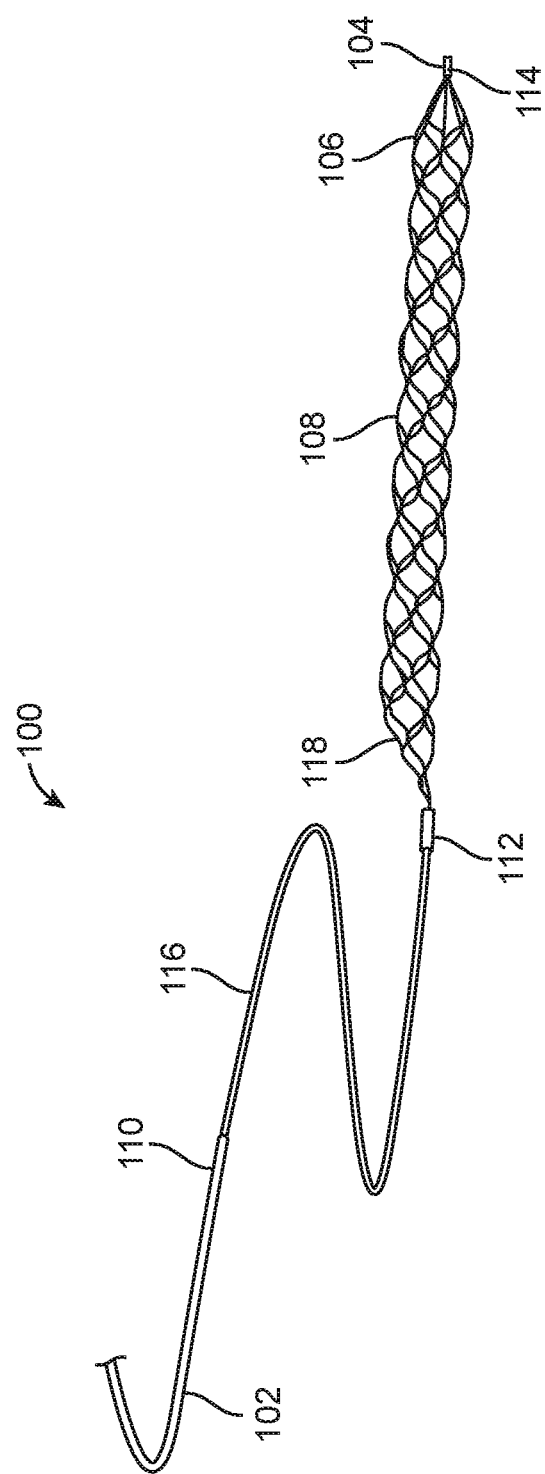
FIG. 1 shows a perspective view of an example of a device for removing obstructions from a patient.

FIG. 1 shows an example of a device 100 for removing obstructions such as blood clots from a patient. This device may be referred to herein as a stent retriever, clot retriever, clot retrieval catheter, or device for removing obstructions. The device 100 may be used to remove clots or other obstructions from a patient, and the device includes a proximal end 102, a distal end 104, a thicker proximal portion of an elongate flexible shaft 110, a thinner distal portion 116 of the elongate flexible shaft and an expandable capture cage 108 that is mesh-like and porous to allow blood to flow through the pores of the cage to avoid causing ischemia, while still maintaining a pore size small enough to ensure that the capture cage can capture the clot or other obstruction without thrombus escaping from the capture cage. The thicker proximal portion of the elongate flexible shaft 110 may be formed from the thinner distal portion 116 of the elongate flexible shaft disposed in a microcatheter or a sheath, or the thinner distal portion 116 of the elongate flexible shaft may simply be thicker to provide a more stiff shaft with better pushability. A proximal end of the expandable capture cage 108 is coupled to a distal end of the thinner portion of elongate flexible shaft 116.

In this example, the elongate shaft is a pusher wire which is also referred to as a guidewire. The proximal portion 110 of the pusher wire may have any cross section but may be round and has a larger diameter than the distal thinner section 116 which may have any cross-section but may also be round and thinner than the proximal section. The thicker proximal section provides better pushability of the device through the vasculature while the thinner distal section provides greater flexibility to navigate tortuous vessels such as in the brain. Once the device has been delivered to the target treatment area the expandable capture cage 108 radially expands either by balloon expansion or by self-expansion. In this example the capture cage is made from a shape memory metal or a super elastic material such as nitinol so that the capture cage is self-expanding. The length of the elongate shaft and sheath constraining the capture cage is dependent on where the treatment region is located in the patient's body and therefore may be any desired length.

Optionally in any example of the device, the proximal and distal ends of the capture cage 108 may include collars 112, 114 to hold the proximal and distal end struts of the capture cage together. The proximal collar 112 may also be used to crimp the proximal end struts of the capture cage to the distal end of the elongate shaft 116, or the collars may be radiopaque markers as discussed below. In some examples the collars are separate cylindrical elements placed over the struts of the expandable cage and the guidewire 116. In other examples the collars may be uncut tubing from which the expandable cage is made and therefore the collars are cylindrical tubes that are integral with the struts of the expandable cage. In any example, the obstruction being treated may be a clot that is disposed in a blood vessel (such as an artery) in the patient's head or anywhere in the body. The proximal end of the capture cage may include a beveled open end 118 that facilitates partial or full proximal retraction of the expandable cage 108 into a sheath or microcatheter if desired. The distal end of the capture cage may include a tapered conical tip 106 that is porous to allow blood to flow through in order to avoid ischemia, while still capturing the clot or other obstruction and preventing the clot from escaping the capture cage. A plurality of struts in the capture cage extend distally and converge to a point to form the tapered tip. Collar 114 may be used to crimp or hold the struts together. As previously mentioned, collar 114 may be a separate cylindrical element or it may be uncut tubing from which the expandable cage is formed and therefore collar 114 is integral with expandable cage 108. Collar 114 also may serve as a radiopaque marker to allow an operator to visualize the distal end the device under fluoroscopy. A number of geometries may be used to form the cells in the capture cage, and examples which may be used are disclosed herein.

Optionally, in any example, the thicker proximal end 102 of the guidewire may be coupled to a handle (not shown) so that the operator can easily manipulate the device during use.

Figure 2:
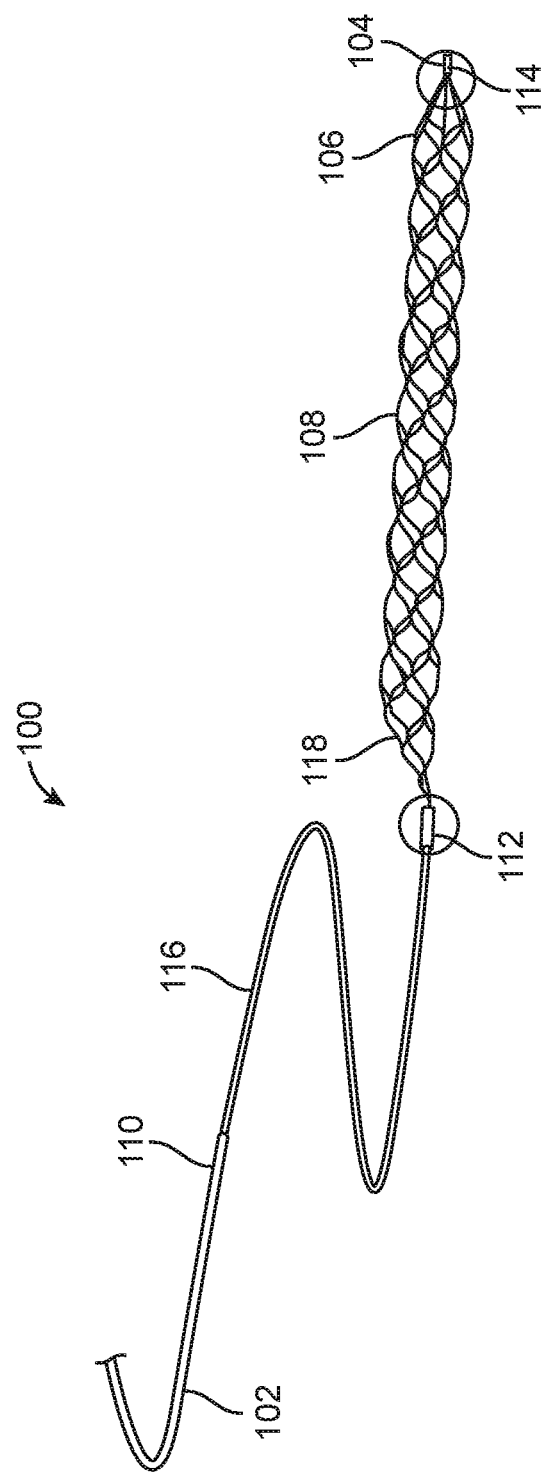
FIG. 2 shows the device of FIG. 1 with optional radiopaque markers.

FIG. 2 shows the same example as FIG. 1 with the difference being that the proximal and distal collars 112, 114 are also radiopaque markers that allow an operator such as an interventional neurologist or radiologist to visualize the ends of the capture cage under fluoroscopy during a procedure to remove obstructions such as clots from a patient. Any high-density material may be used as a radiopaque marker such as platinum, gold, or other materials known in the art. The collars 112, 114 may also be used to help crimp the struts of the capture cage together or to couple the struts to the distal end of the elongate shaft 116 or form the tapered distal tip. The collars may also be uncut tubing from which the expandable cage is formed and therefore the collars are integral with the struts of the expandable cage, as previously discussed. Other aspects of FIG. 2 are generally the same as FIG. 1. The use of radiopaque markers in this example is optional, and the radiopaque markers disclosed here may be optionally used in any example of a capture cage disclosed herein.

FIG. 3A shows a side view of the expandable capture cage 300 that may be used in any of the examples of obstruction removal devices disclosed herein. The expandable capture cage 300 is shown in the expanded configuration and includes a proximal end 302 which is coupled to the distal end of the elongate shaft (not shown in FIG. 3A) which may be a guidewire or other elongate shaft, so the device may be advanced through the patient's vascular system to a target treatment region and then retracted and removed upon completion of the procedure. The proximal end 302 may include an open beveled end as previously described above and as will be further described elsewhere in this disclosure. The expandable capture cage 300 also includes a distal end 306 which may also include the tapered conical distal tip 308 formed from several struts extending distally from the distal end of the expandable capture cage and converging to a point. The tapered conical distal tip 308 serves as a distal filter trap to prevent clots or other debris from exiting out of the distal end of the expandable capture cage and has sufficient porosity due to the apertures between the struts to allow blood to flow through the tapered conical distal tip (thereby avoiding causing ischemia) but the apertures are small enough to minimize or prevent clots or other debris from passing therethrough. The gap between struts in the tapered conical distal end may have any size but optionally in any example may be less than 3 mm, 2.5 mm, 2 mm, or any other size. Strut thickness or width in the tapered conical distal end may be thicker, thinner or the same compared to the struts in the main body of the expandable cage. The main body 310 of the expandable capture cage is substantially cylindrically shaped and includes interconnected struts 314 which form closed cells. The apertures in the closed cells that form the wall of the cage are similarly are porous enough to allow blood flow therethrough to prevent causing ischemia while still capturing and preventing clots or other debris from passing through the side wall of the expandable cage. The expandable cage includes a number of circumferentially oriented rings 312 which extend axially along the longitudinal axis of the expandable cage to form the cage. The struts 314 form closed cells in each ring and the ring may be fully closed or the edges of the ring may not be joined together thereby forming an open ring with a gap between the edges of the ring. For example, in the example of FIG. 3A, in the proximal beveled region of the expandable cage, at least the first two rings are open rings while the rest of the rings in the body of the expandable cage are closed rings and the distal conical tip has its own configuration with linear struts converging to a point to form the tapered tip. Adjacent rings may be coupled together to form the cylindrical tube that is the expandable cage and adjacent closed cells may share a common strut. In this example, the closed cells are lemon shaped and each lemon shaped closed cell is formed by connecting several sigmoidally shaped and inverse sigmoidally shaped struts together to form the peak and valley of the lemon shape as well as pointed proximal and distal end of the lemon shape. Additional disclosure related to the cell geometry is disclosed in this specification. Each strut has a thickness which is generally related to the wall thickness of the hypodermic tubing used to form the cage by laser cutting, photoetching, electrical discharge machining or other techniques known in the art. The strut thickness along the cage may be the same, or strut thickness may vary in order to provide varying mechanical properties along the length of the cage, such as providing stiffer regions and more flexible regions. Strut thickness maybe varied by grinding, electropolishing or using other processes known in the art. Similarly, the strut length and width may also be constant along length of the cage or they may vary in different regions to provide regions with desired mechanical properties. For example, the proximal struts in a cell may be thicker than other struts in a cell to provide a stiffer edge and more support as well as providing more surface area for better engagement and enmeshing of the cage with the clot.

Figure 3B:
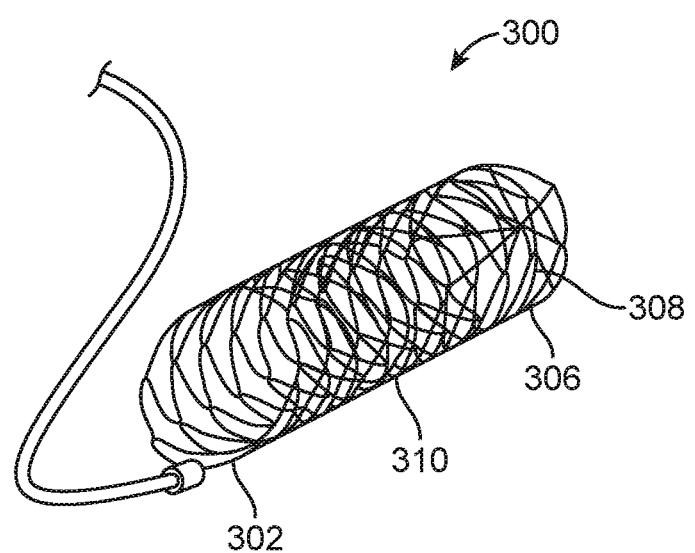
FIG. 3B shows a perspective end view of the cage in FIG. 3A.

FIG. 3B shows a perspective end view of the proximal end of the expandable cage 300 in FIG. 3A and highlights the open proximal end with the tapered bevel which is described in further detail in the flat pattern of FIG. 4A below. Other aspects of FIG. 3B generally take the same form as in FIG. 3A. FIG. 3B also shows the elongate shaft coupled to the proximal end of the expandable capture cage with the collar.

Figure 4A:
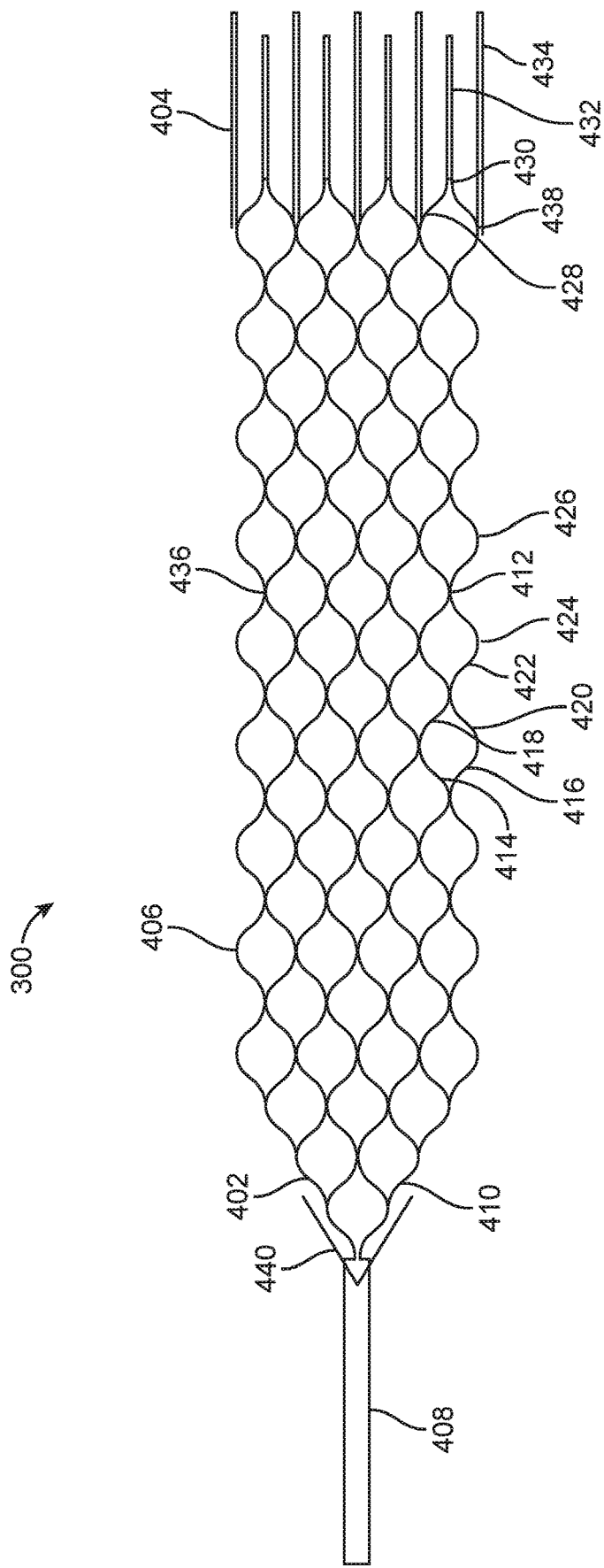
FIG. 4A illustrates the expandable capture cage of FIG. 3A shown in a flat unrolled configuration.

FIG. 4A shows the stent retriever device (also referred to a clot retriever or device for removing obstructions) of FIG. 3A but with the expandable capture cage in the unrolled and flat configuration for ease of viewing the cell geometry. The expandable capture cage 300 has a proximal end 402 and a distal end 404 and an intermediate portion (also referred to as central portion or central body) or body 406 disposed therebetween. The proximal end 402 is coupled to the elongate shaft 408 which may be a guidewire or the collars previously discussed which can include optional radiopaque marker bands or separate cylindrical collars or uncut tubing collars may be coupled to the proximal and distal ends 402, 404 to help identify the ends of the expandable cage under fluoroscopy during use.

The central body 406 of the expandable capture cage includes a plurality of circumferentially oriented rings 424, 426 that are coupled together at a connection point 412. The space between adjacent coupled rings 424, 426 may also be considered to be a ring 436 although one of skill in the art will appreciate that this ring is formed by coupling the adjacent rings and thus the struts in the cells of ring 436 are shared with the cells in the adjacent rings with a common border. Each ring in the central body 406 may be a closed ring formed from a plurality of closed cells 422. The device may have any number of rings to create a capture cage of desired length to accommodate the treatment region. Similarly, the diameter of the closed cells may be adjusted to provide an expandable capture cage of appropriate diameter to treat differing vessel sizes. In this example the rings 424, 426, 436 in the central body 406 each have four closed lemon shaped cells, although this is not intended to be limiting and the number of closed cells may be varied. Each lemon shaped closed cell is formed from four struts 414, 416, 418, 420, two sigmoidally shaped struts 414, 420 (from proximal to distal direction) and two inverse sigmoidally shaped struts 416, 418 (from proximal to distal direction) coupled together to form the lemon shape. The sigmoidally shaped struts 414, 420 have a compound curve with a concave region facing outward away from the center of the closed cell and a concave region facing inward toward the center of the closed cell. The inverse sigmoidally shaped struts 416, 418 have compound curves with a concave region facing inward toward the center of the closed cell and a concave region facing outward away from the center of the closed cells. In this example, a first sigmoidally shaped strut is followed by an inverse sigmoidally shaped strut followed by a sigmoidally shaped strut followed by an inverse sigmoidally shaped strut in the clockwise direction. Thus the closed cell has a concave outward region followed by a concave inward region followed by a concave inward region followed by a concave outward region followed by a concave outward region followed by a concave inward region followed by a concave inward region followed by a concave outward region in the clockwise direction. Opposite ends of the struts are coupled together to close the cell. Each cell is expandable thereby imparting radial expansion to each ring in the cage. The cage may be balloon expandable or may be formed using superelastic or shape memory alloys such as nitinol, so the cage is self-expanding. The lemon shaped closed cell has a flaring proximal end and a tapering distal end. The proximal flare begins at a proximal point and flares to a maximum cell width, and the distal taper begins at the maximum cell width and tapers down to a distal point. Each lemon shaped closed cell also includes a peak at the superior portion of the closed cell which is at maximum width and a valley or trough at the inferior portion of the cell also at the maximum width position. The peaks and valleys are generally located in between the proximal and distal points of the closed cell. The proximal and distal ends of the lemon shaped cells have a pointed region extending in the respective proximal or distal direction.

The proximal end 402 of the cage may have an open beveled end 410. This is formed by reducing the number of closed cells in each ring moving proximally so the rings transition from fully closed rings to open rings. Here, the last closed ring has four closed cells, then an open ring of three closed cells, followed by an open ring of two closed cells followed by an open ring of one closed cell, all of which are shaped to form a wall of the cylindrically shaped cage. Thus, the wall is fully closed due the fully closed ring of four closed cells and then the wall is partially open and increasingly open moving proximally from the open rings of three closed cells to two closed cells to one closed cell. The open gap between edges of the open rings will increase in the proximal direction because there are less and less closed cells forming each ring. The angle 440 formed by the edges of the proximal struts may be any angle but in this example is less than 90 degrees, or it may be less than or equal to 60 degrees, or less than or equal to 45 degrees, or less than or equal to 30 degrees. The angle in any example may be greater than or equal to zero degrees and have a maximum angle less than 90 degrees, or less than or equal to 60 degrees, or less than or equal to 45 degrees, or less than or equal to 30 degrees.

As also discussed, the distal end 404 in this example is a tapering distal tip or distal trap formed from several linear struts that extend distally from the distal end of the cage and converge radially inward to a point where their ends are twisted, tied, crimped, bonded, welded or otherwise coupled together to form the porous distal tapered tip. The linear struts 432, 434 may be longer or shorter relative to one another depending on where they are coupled to on the distal end of the cage as a mechanism for accommodating differing amounts of foreshortening on the cage. For example, a short strut 432 may be coupled to the distal pointed portion 430 of the lemon shaped closed cell and a longer strut 434 may be coupled to the inferior or superior portion 438 (also may be referred to as a peak or valley or maxim width portion of the cell) of the lemon shaped cell. The pointed portion 430 moves an axially different amount than the inferior or superior portion 438 during expansion or contraction of each cell during radial expansion of the cage, and therefore the different lengths accommodate for this different amount of foreshortening and maintain an even shape of the tapered distal tip. In other examples, the struts in the distal tip may be coupled to a middle portion 428 between the distal point and the peak or valley of the lemon shaped closed cell.

Figure 4B:
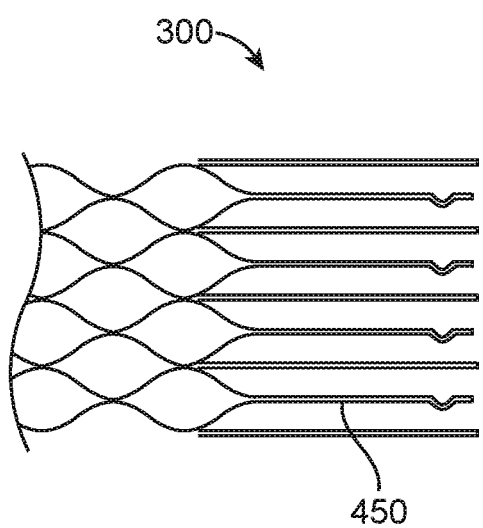
FIG. 4B shows the expandable cage flat of FIG. 4A in the flat and unrolled configuration with arcuate struts in the distal tapered tip.

FIG. 4B shows only the distal portion of the expandable cage 300 in FIG. 4A. The major difference being the use of arcuate struts 450 in the distal tapered tip. Here, arcuate struts 450 may be coupled to the pointed distal portion of the lemon shaped cells, or they may be coupled to any other portion of the closed lemon shaped cell as described herein. The arcuate struts include a long linear portion that is coupled to the distal-most closed cell and a curved distal portion. The curved distal portion may be undulating, S-shaped, sinusoidal, meandering, or any other pattern that allows axial expansion and contraction of the strut 450 during radial expansion and collapsing of the expandable cage. Therefore, the undulating struts help accommodate for foreshortening of the cage during expansion and contraction. Other aspects of the expandable cage may be the same as in FIG. 4A or features from other examples of expandable cages may be used in combination with or substituted for the features of FIG. 4A. The struts described in FIG. 4B may optionally be used in any of examples of capture cages disclosed herein.

Figure 5:
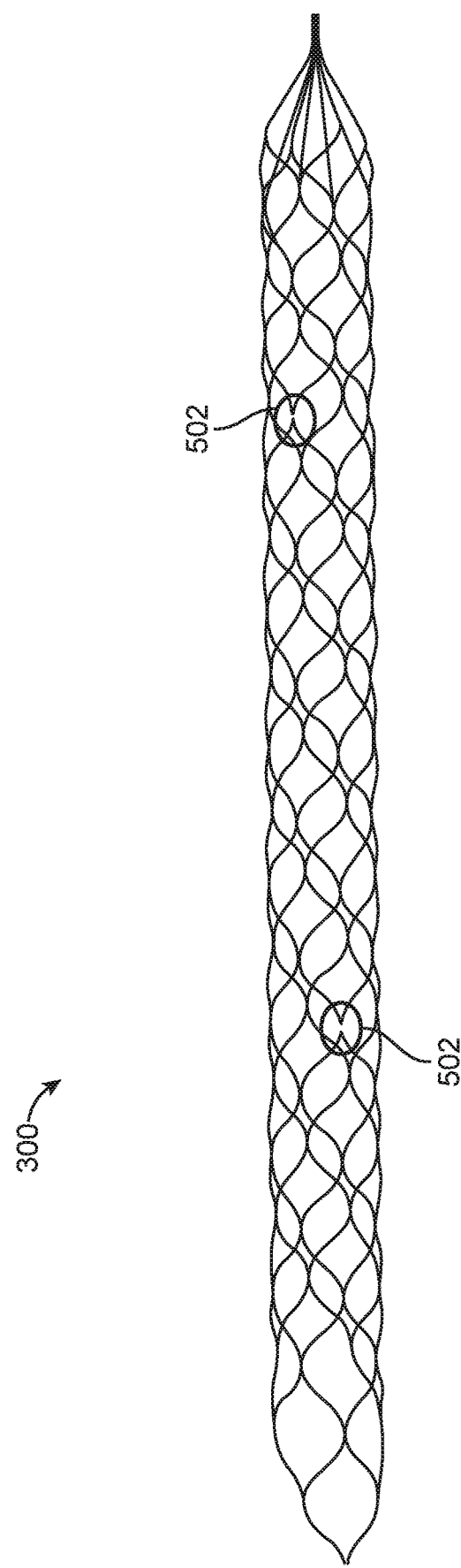
FIG. 5 shows the expandable capture cage of FIG. 3A with optional flexible regions.

FIG. 5 shows an example of an expandable capture cage 300 that is the same as previously shown in FIG. 3A with the only difference being that expandable capture cage 300 includes optional flexible regions 502 in the capture cage. The flexible regions may be disposed anywhere along the length of the expandable cage for example, in the middle (half way between proximal and distal ends of the expandable cage), ⅓ of the length of the expandable cage and closer to the proximal end of the cage, or ⅔ of the length of expandable cage and closer to the distal end, or any other location. In the case of the flexible region in the middle, two cage segments are formed, while in the case where a flexible region is disposed ⅓ of the length of the cage and ⅔ of the length of the cage, three segments are created. This is not intended to be limiting and any number or any position of flexible joint may be employed. A flexible joint may be disposed anywhere circumferentially along the expandable cage, for example assuming the cross section of FIG. 5 is represented by a circle and a clock is superimposed on the cross-section, section, the flexible joint may be at one or more positions such as 1, 2, 3, 4, 5, 6, 7, 8, 9, 10, 11, or 12 o'clock. As an example, two flexible joints maybe disposed at the top and bottom of the cage at the 12 and 6 o'clock positions, or the 3 and 9 o'clock positions. The flexible regions are formed by creating a disconnection or gap between adjacent closed cells at the proximal or distal pointed portion of the adjacent lemon shaped cells. In the example of FIG. 5, there are two flexible regions formed by decoupling adjacent closed cells. Each flexible region allows the portions of the expandable cage on either side of the gap to flex relative to one another thereby creating the flexible region. This allows greater bending during delivery through tortuous vessels or allows the expandable cage to more easily conform to the local contours of the anatomy. Additionally, when the expandable cage is constrained by a sheath and then partially retracted, the flexible regions allows full expansion of the distal portion of the expandable cage that has been unsheathed. The flexible region may be formed by cutting the connection point between adjacent closed cells to form the gap or discontinuity. The cutting may be accomplished during manufacturing of the expandable cage, or it may be performed by a physician operator just before delivery in a patient and may be customized as needed. The flexible regions may be disposed in any position circumferentially around each ring of the expandable cage, or in any axial position along the longitudinal axis of the expandable cage and thus the expandable cage can have any number of flexible regions. Strut width or thickness adjacent the gaps, or at adjacent connection points may be greater than other struts in order to provide increased strength around the gap. Radiopaque markers may be disposed adjacent the gaps so that an operator can visualize the flexible regions under fluoroscopy. Other aspects of the expandable cage are generally the same as the example in FIG. 3A. Thus, flexible joints may be optionally combined with or substituted with any of the features disclosed with respect to the example in FIG. 3A or any of the examples of expandable cages disclosed herein.

FIG. 6A shows another example of an expandable capture cage 300 that is the same as previously shown in FIG. 3A with the only difference being that expandable capture cage 300 optionally includes thinner struts on the open beveled proximal region. The struts 606 in the body of the expandable cage have a certain thickness and width. Thickness is generally dictated by the wall thickness of the tubing from which the expandable cage is cut although this may be controlled by grinding, electropolishing, or other methods known in the art. And strut width is controlled by the laser or other tube cutting process. In the example of FIG. 6A, the struts 604 in the proximal open beveled region 608 (sometimes also referred to as a proximal taper) may have a thickness or width that is less than that of the struts 606 in the main body of the expandable cage. For example, strut width may be 20 to 50 microns in the proximal portion. The reduced thickness or width of struts in the proximal portion of the cage allow the proximal end of the cage to collapse more easily due to reduced radial strength and therefore the expandable cage can be more easily retracted into the sheath or microcatheter if re-sheathing is performed. The proximal open beveled region 608 is coupled to the distal portion of an elongate shaft 602 such as a guidewire. Other aspects of the expandable cage 300 in FIG. 6A are substantially the same as the example in FIG. 3A. Thus, the reduced strut dimensions described with respect to FIG. 6A may optionally be used in conjunction with or substituted for any of the features in the example of FIG. 3A or any of the other examples of expandable cages disclosed herein.

Figure 6B:
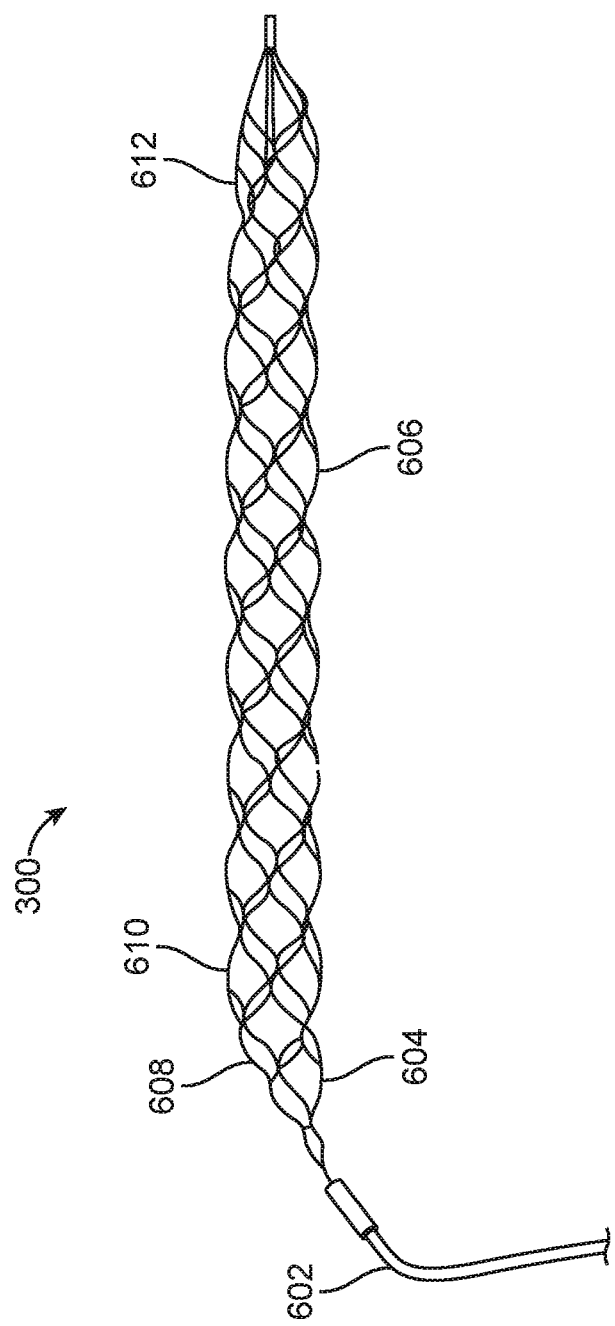
FIG. 6B shows the expandable capture cage of FIG. 3A with a taper.

FIG. 6B shows another example of an expandable capture cage 300 that is the same as previously shown in FIG. 3A with the only difference being that expandable capture cage 300 optionally is tapered along its length. A portion of the expandable capture cage may be tapered, or the entire length of the capture cage may be tapered. Tapering allows the capture cage to match the vessel anatomy better thereby allowing better apposition of the cage with the vessel wall. In this example, the diameter 610 of the proximal end of the cage in the expanded configuration is larger than the diameter 612 of the distal end of the capture cage in the expanded configuration. Other aspects of the catheter and capture cage are substantially the same as previously described with respect to previous examples including FIGS. 3 and 6A, including the elongate shaft 602, optional varying strut dimensions 604, 606 (described with respect to FIG. 6A), proximal bevel 608, etc. Therefore, any of the features disclosed in FIG. 6B may be used in combination with or substituted for any of the features for any of the other expandable cages disclosed herein.

Figure 7:
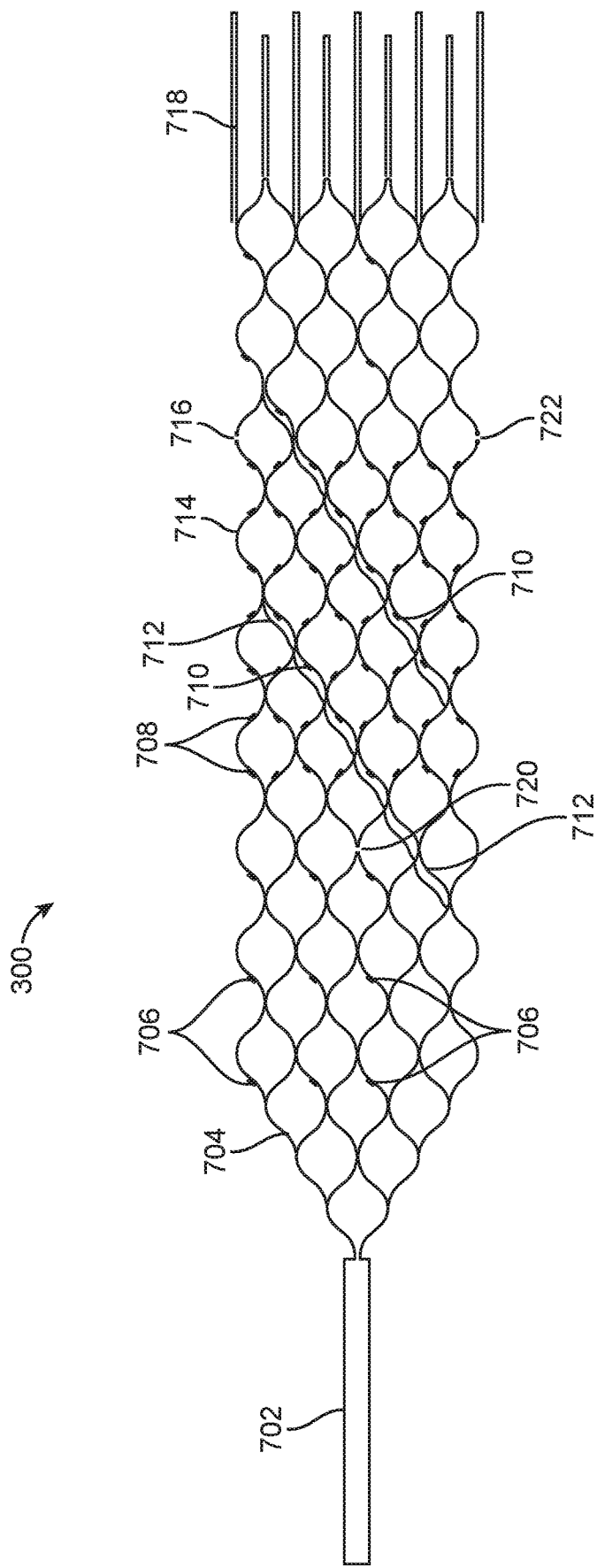
FIG. 7 shows the expandable capture cage of FIG. 3A in an unrolled and flat configuration and with optional double struts and optional radiopaque markers.

FIG. 7 shows another example of an expandable cage that may be used with any device for removing obstructions from a patient disclosed herein. The expandable cage 300 is the same as that shown in FIG. 3A with the major differences being that the cage 300 in FIG. 7 includes an optional double strut region and optional radiopaque markers that may be used in any example of expandable cage disclosed herein.

The expandable cage 300 shown in FIG. 7 is the same as previously shown in FIG. 3A with the major differences being the use of an optional double strut, an optional flexible region, and optional radiopaque markers. The double strut provides greater stiffness and strength along that edge of the cell with the double strut and also due to increased surface area helps enmeshing and clot removal as well as improving visualization under fluoroscopy. FIG. 7 shows an expandable cage that has been unrolled and flattened out. The expandable cage 300 has a proximal tapered or beveled edge 704 that is coupled to an elongate shaft 702 which may be a guidewire with or without any of the collars previously described. Other aspects of the proximal tapered edge are substantially the same as previously discussed with respect to FIG. 3A. Similarly, the distal portion 718 of the cage is also the same as the distal portion of the cage in FIG. 3A, including the tapered distal cone or tip that serves as a trap to prevent clots or other debris from exiting the cage while still allowing blood flow therethrough.

The struts of the expandable cage include radiopaque markers to help the physician operator visualize the cage under fluoroscopy during a procedure. The radiopaque markers may be located anywhere along the cage. For example, the proximal end of the cage may include a radiopaque marker 706 on a proximal strut of a closed cell, although this is not intended to be limiting. Each ring may include radiopaque markers or other radiopaque marker patterns may be used. In this example, which is not intended to be limiting, a radiopaque marker is located on a proximal sigmoidal strut of a closed lemon shaped cell, and each ring includes at least two closed cells with a radiopaque marker with an unmarked closed cell disposed therebetween. An adjacent ring may have the same radiopaque marker pattern so that the radiopaque markers extend in a linear array along the longitudinal axis of the cage. The ring that is formed by two adjacent rings being connected together (e.g. the ring with cells that share struts with adjacent cells) may or may not include a radiopaque marker, and in this example, there is no marker in that ring.

The distal portion of the expandable cage may have the same pattern of radiopaque markers as the proximal portion, or it may have a different pattern. The middle portion 714 of the expandable cage which may be ½, or ⅓, or ¼ of the length of the cage may have a denser pattern of radiopaque markers 708. Here the radiopaque markers 708 are increased on each closed cell. For example, here at least some of the closed cells in the middle portion include four radiopaque markers 708, one on each strut of the four struts (two sigmoidally shaped and two inverse sigmoidally shaped struts) which make up the closed cell. This helps ensure that the expandable cage is aligned with the clot or other obstruction to be removed from the patient. Also, because the cage self-expands into engagement with the vessel wall, having additional markers helps the operator visualize the overall three dimensional shape of the expanded cage which will reflect any abnormality in the vessel wall such as plaque that may indent or prevent full expansion of the cage.

FIG. 7 also shows the use of optional flexible regions 716, 720, 722 which have been previously described. Flexible regions are formed by leaving adjacent closed cells uncoupled to form a gap therebetween to allow the cage to flex around the gap. Here, the flexible regions include two flexible regions (716 and 722 are the same flexible region) and they are disposed in the middle portion of the cage, although they may be located anywhere along the cage and any number may be used.

The example in FIG. 7 also optionally includes a double parallel strut 712 that runs diagonally along the flat view but in the rolled up cylindrical view of the cage the double strut will appear as a helix around the cylindrically shaped cage. The double strut may also be formed by a several sigmoidally shaped struts connected together along the helical line in the rolled up cylindrical view (diagonal line in the unrolled view). Here there are optionally two double strut regions. The double strut region provides two stiffer regions of the cage and also stiffer edges to help the cage expand into a clot or obstruction and also provides a stiffer edge that can slide through the clot or obstruction to sever it when the cage is being advanced or retracted. A small slit or gap is disposed between the double struts. Optionally, in this example, the double struts may also include radiopaque markers 710 on one or both of the double struts to facilitate visualization under fluoroscopy during a procedure.

Other aspects of expandable cage 300 in FIG. 7 are generally the same as previously described in FIG. 3A or any of the other cage examples disclosed herein. Any of the features disclosed with respect to FIG. 7 may be used with or substituted for any of the features described in FIG. 3A or any other example of expandable cage disclosed herein. Thus, optionally an expandable cage may include any permutation or combination of the cell geometries, any of the radiopaque marker patterns, any of the strut dimensions, any of the proximal bevel features, any of the distal tapered tip features, double struts patterns, flexible region patterns, elongate shaft features, etc.

FIGS. 8A-8I illustrate an example of treating a patient suffering a stroke due to a blood clot in an artery of the brain. This is not intended to be limiting and one of skill in the art will appreciate that the devices and methods disclosed herein may be used to treat clots or obstructions in other parts of the vessels of the body.

Figure 8A:
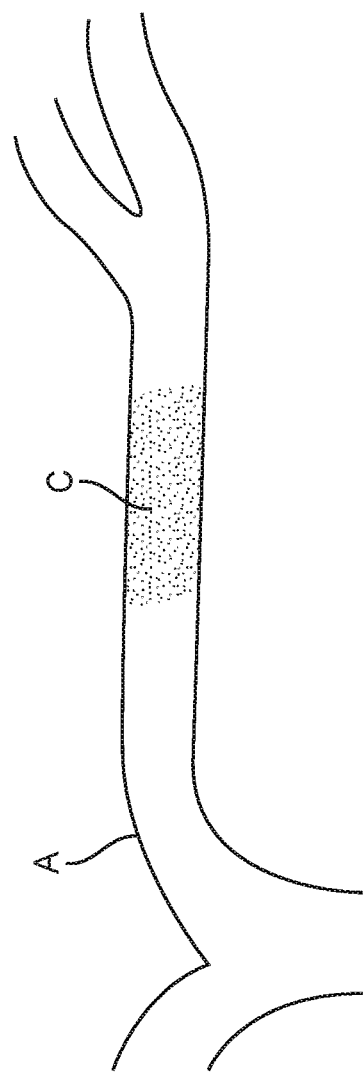

In FIG. 8A, an artery A of the brain is shown with a blood clot C occluding the vessel preventing or limiting oxygenated blood from flowing past the blockage thereby causing a stroke due to ischemia. The clot may fully or partially occlude blood flow through the vessel.

Figure 8B:
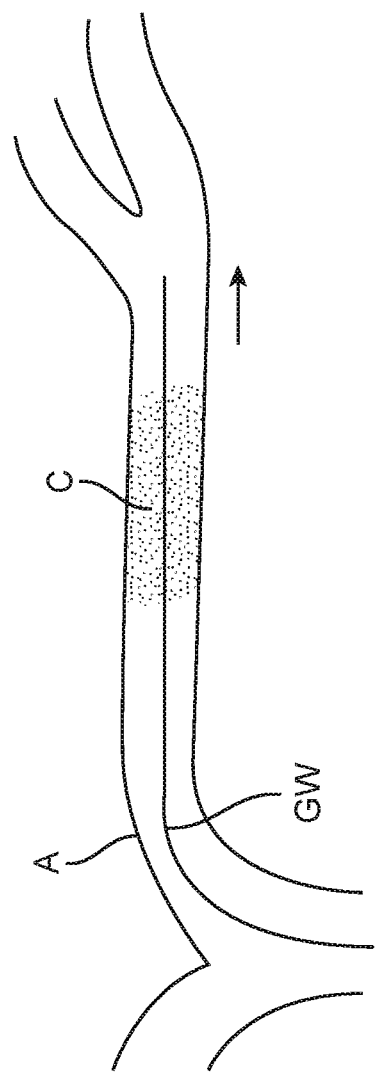

In FIG. 8B, a guidewire GW is introduced percutaneously into a blood vessel typically an artery, and advanced through the vessel, through the clot and distal of the clot. The guidewire may be introduced percutaneously into a vessel using standard procedures such as the Seldinger procedure or using a surgical cut down. Examples of access points may include the groin, the wrist, the neck, etc. and the guidewire may be advanced in any artery (e.g. femoral artery, carotid artery, radial artery, etc.) or any vessel such as a vein using known access techniques.

Figure 8C:
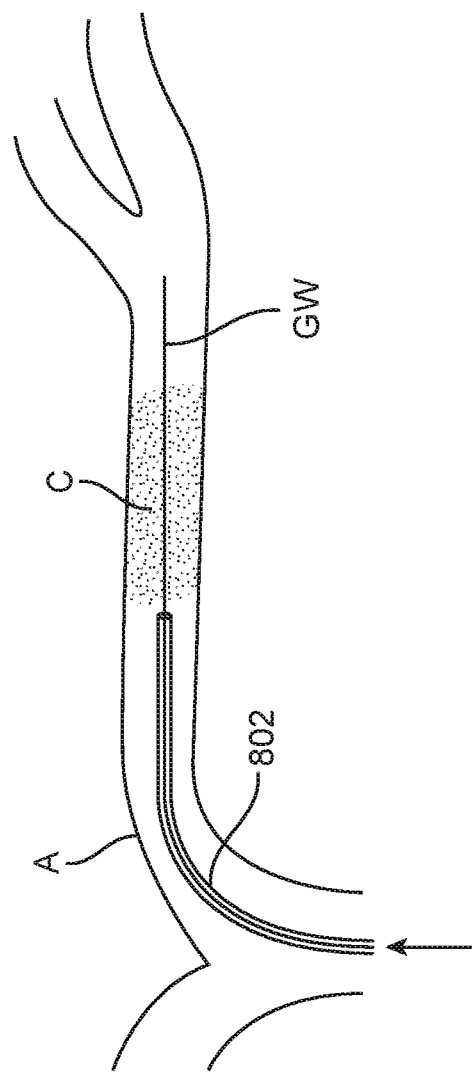

Once the guidewire is in place, it acts as a rail over which a microcatheter may be advanced to the treatment site. In FIG. 8C, a microcatheter 802 with a lumen is advanced distally in the affected artery A over the guidewire GW to the clot C. The microcatheter may be a single lumen catheter that provides a tunnel through which a stent retriever catheter (sometimes also referred to herein as a clot retriever or device for removing obstructions) may be advanced through the vasculature to the treatment site. The size of the microcatheter may be selected based on the vessel being treated.

Figure 8D:
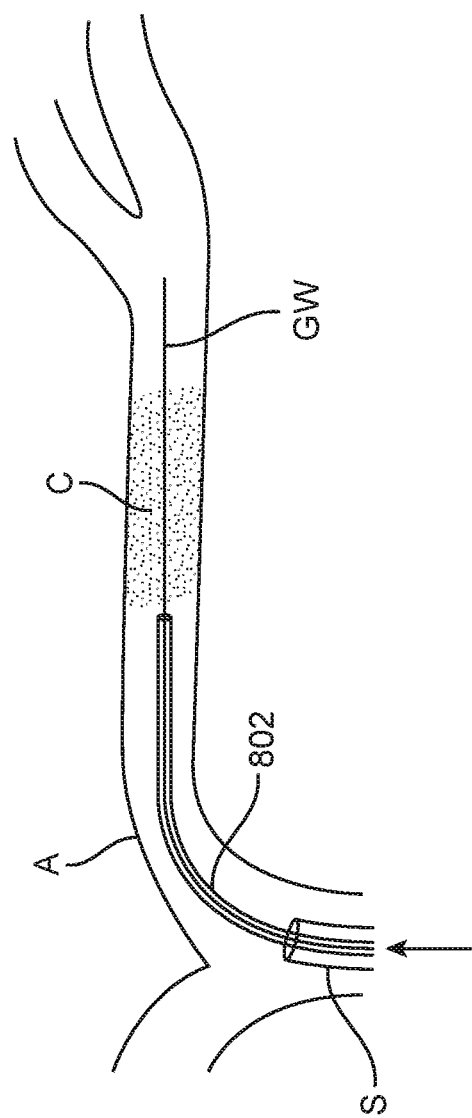

FIG. 8D shows optional use of a sheath S. Here, after the guidewire is inserted, a sheath (e.g. a guide sheath) may be advanced over the guidewire GW. The microcatheter is then advanced over the guidewire GW and through a lumen of the sheath S until the microcatheter is adjacent or abuts the clot C. Thus, if a sheath is used, FIG. 8D replaces FIG. 8C. Once the microcatheter has been properly advanced and positioned, the sheath may either remain in place, be retracted proximally to move it out of the way but remain in the vessel, or the sheath may be entirely removed from the vessel.

Figure 8E:
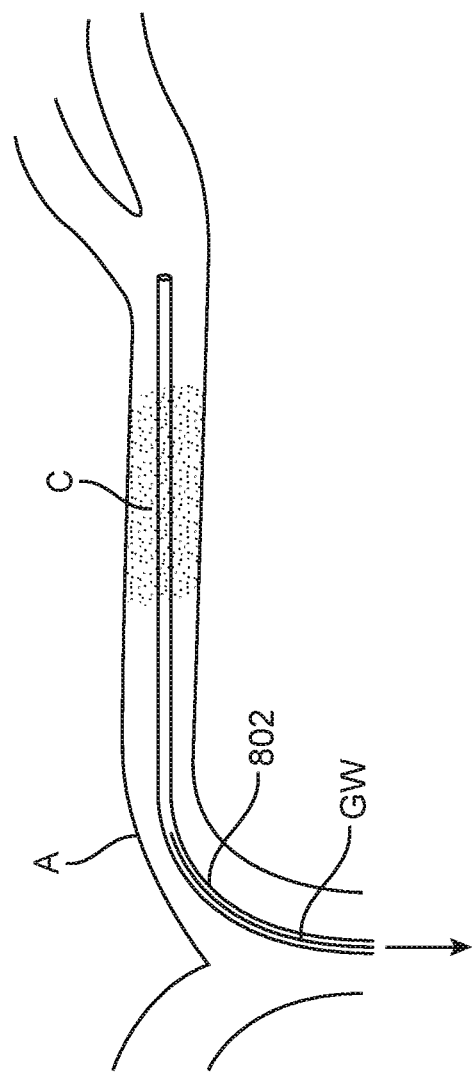

In FIG. 8E, the microcatheter 802 is advanced through the artery A so that its distal tip passes through the clot and is distal of the clot C. The guidewire GW is retracted proximally and may be removed from the patient.

Once the microcatheter has been positioned, a stent retriever catheter such as any of those disclosed herein may introduced through a port of an introducer (not shown) at the vascular access point and advanced through the microcatheter toward the treatment region. An outer sheath (not shown) may be disposed over the stent-retriever catheter for packaging and shipping purposes as well as to constrain the expandable cage. Thus, once the stent retriever has been inserted into the microcatheter, the outer sheath on the stent retriever may be proximally retracted and removed from the expandable cage. The microcatheter then constrains and prevents the expandable cage from self-expanding.

Figure 8F:
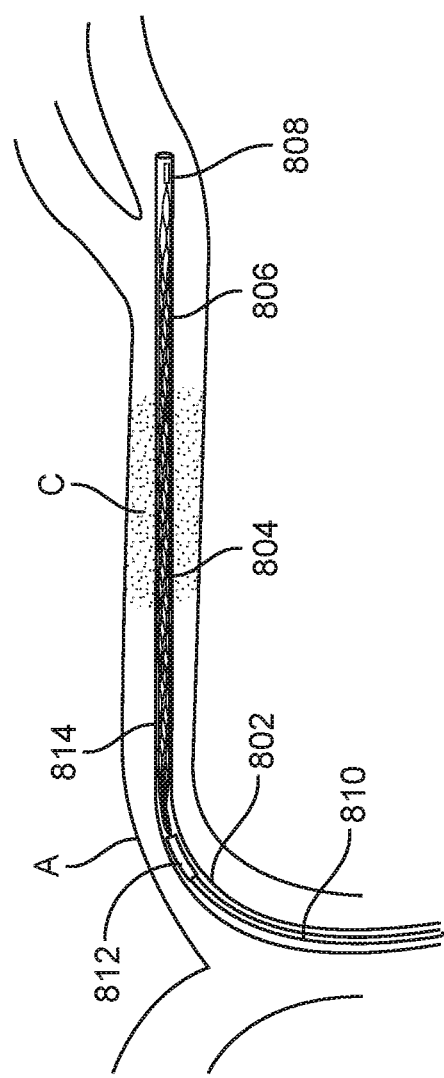

FIG. 8F shows the clot retriever catheter 806 disposed in the microcatheter 802 and traversing the clot C. The clot retrieval device 806 is shown including the distal portion of the expandable cage traversing the clot C, the expandable capture cage 804, elongate shaft 810, optional proximal radiopaque marker or collar 812 and optional distal radiopaque marker or collar 808. The clot retriever catheter 806 may be any of the examples disclosed herein.

The micro catheter 802 not only provides a channel for delivering the clot retrieval catheter 806 but also provides a constraint that holds the expandable capture cage 804 in a collapsed configuration during delivery. Optional proximal and distal radiopaque markers 808, 812 allow the operator to visualize the position of the device and ensure that the expandable capture cage is disposed along the entire length of the clot C. Elongate shaft 810 is a guidewire coupled to the expandable capture cage and allows the operator to push or pull the device along the artery A and through the microcatheter relative to the clot C. The expandable capture cage may include any or all permutations or combinations of capture cage features described in any example in this specification.

Figure 8G:
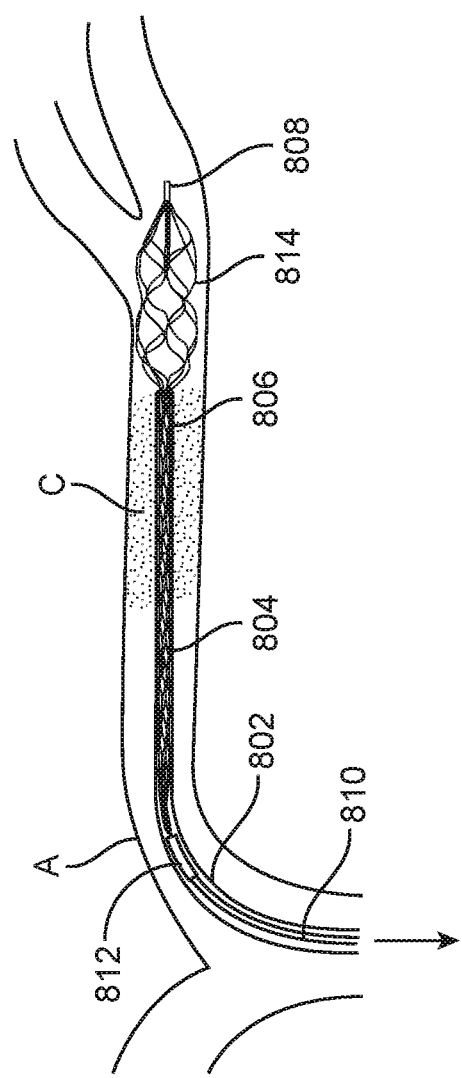

Once the capture cage 804 has been properly positioned relative to the clot C, the microcatheter 802 is retracted proximally as shown in FIG. 8G while the clot retrieval catheter remains stationary or is advanced slightly out of the microcatheter. As the microcatheter 802 is removed from the expandable capture cage 804, it self-expands 814 into engagement with the clot C and the vessel wall. Because the walls of the capture cage are formed from closed cells, the walls of the cage are porous with apertures extending through the wall creating a mesh-like cage wall which can expand into the clot C and enmesh the clot so that the clot is disposed inside the cage and the struts of the cage are outside or mostly outside of the clot. FIG. 8G shows partial expansion of the distal portion of the cage that extends beyond the clot.

Figure 8H:
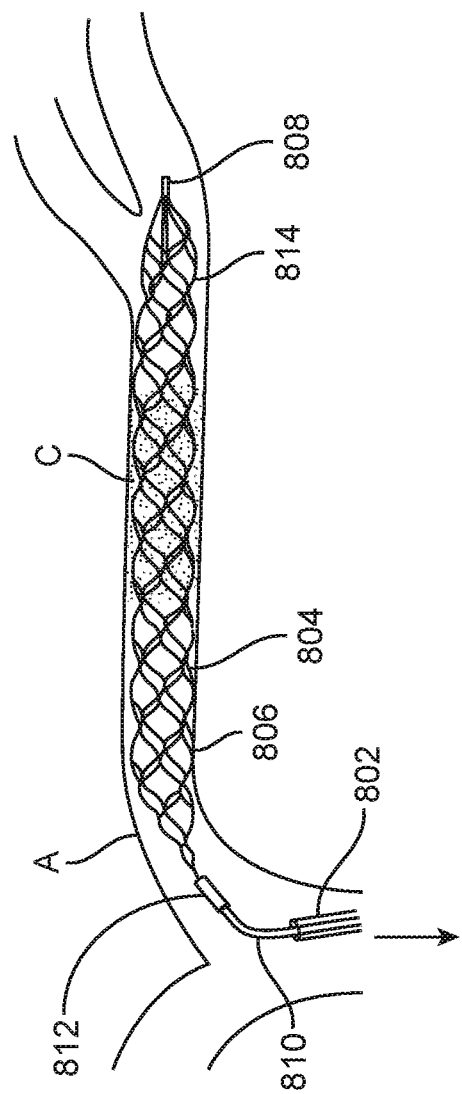

In FIG. 8H, further proximal retraction of the microcatheter 802 unsheathes the entire capture cage so it can self-expand and enmesh the clot C thereby integrating the clot with the expandable cage. The capture cage may self-expand into apposition with the walls of the vessel. The entire clot C is now substantially in the expanded capture cage 814.

Figure 8I:
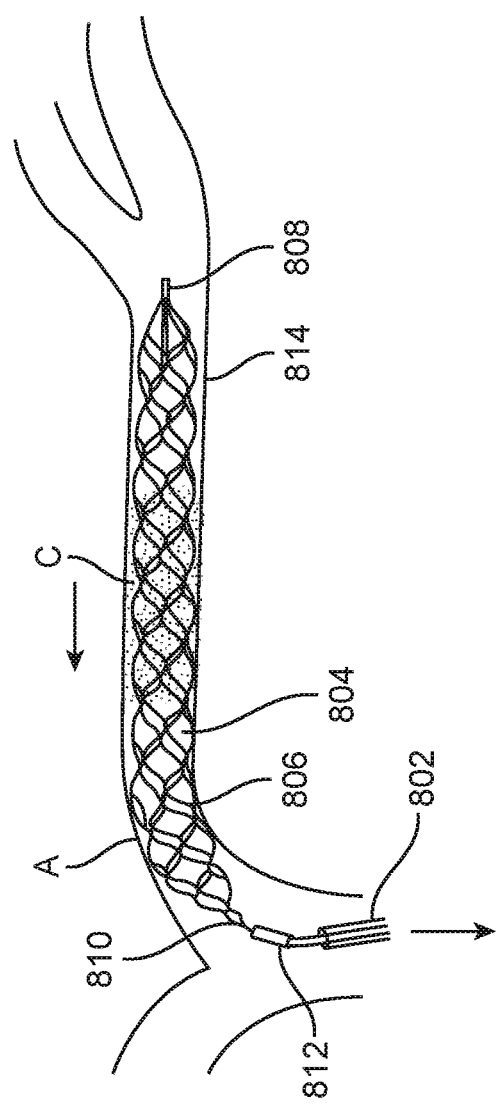

FIG. 8I shows that once the cage 814 has self-expanded and enmeshes the clot C, the entire clot retrieval device 806 is proximally retracted by pulling on the elongate shaft 810 which extends proximally outside of the patient's body so that an operator may grasp and manipulate the proximal end. Proximal retraction of the catheter also carries the enmeshed clot C with the cage 814 as it is retracted proximally. The catheter 806 and clot along with the microcatheter 802 are then retracted proximally until they are removed from the patient. The expandable cage 814 may be retracted proximally so that the proximal end of the expandable cage approximates the distal end of the microcatheter, or the two ends may remain separated from one another. Both the microcatheter and the elongate shaft 810 of the clot retrieval catheter may be retracted proximally together or individually.

FIG. 8J shows the optional sheath S that may have been used to help deliver the clot retrieval catheter (see FIG. 8D). After the clot has been enmeshed in the cage 814, the microcatheter and the cage 814 may be retracted proximally into the sheath S and everything removed from the patient. Or optionally, the microcatheter and cage 814 may be retracted proximally partially and adjacent the distal end of the sheath S, but not necessarily all the way into the sheath S and then everything may be removed from the patient.

Figure 8K:
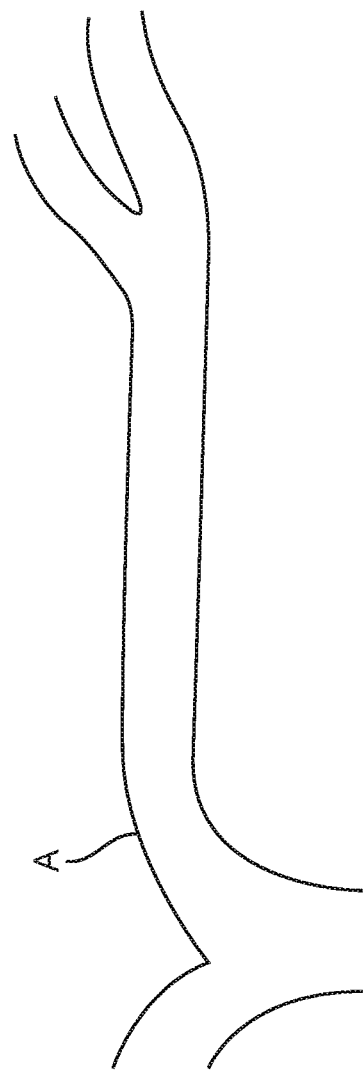

FIG. 8K shows the artery after the clot, microcatheter, optional sheath, and clot removal device have been removed from the artery A. The vessel is now patent again once the obstruction has been removed and tissue downstream of the clot will now receive oxygenated blood.

The procedure ideally is performed as quickly as possible. In any example 5, 4, 3, 2, or 1 minute(s) may be allowed for the clot to integrate into the expanded cage following expansion thereof and before the device is retracted proximally to remove the clot.

The example of a method shown in FIGS. 8A-8K are illustrated with respect to clot removal from an artery in the brain during a stroke. However, this is not intended to be limiting and the method may be applied to removing obstructions from other parts of the body including clots in other arteries of the body or other vessel obstructions. Additionally, the clot retrieval device shown in FIGS. 8A-8K may be any of the devices disclosed herein with any of features used in any permutation or combination. Therefore, any expandable cage may be used with any feature such as radiopaque markers, lemon shaped closed cell geometry, flexible regions, double struts, tapered or beveled proximal end and tapered distal tip, as well as any of the strut configurations.

Figure 9:
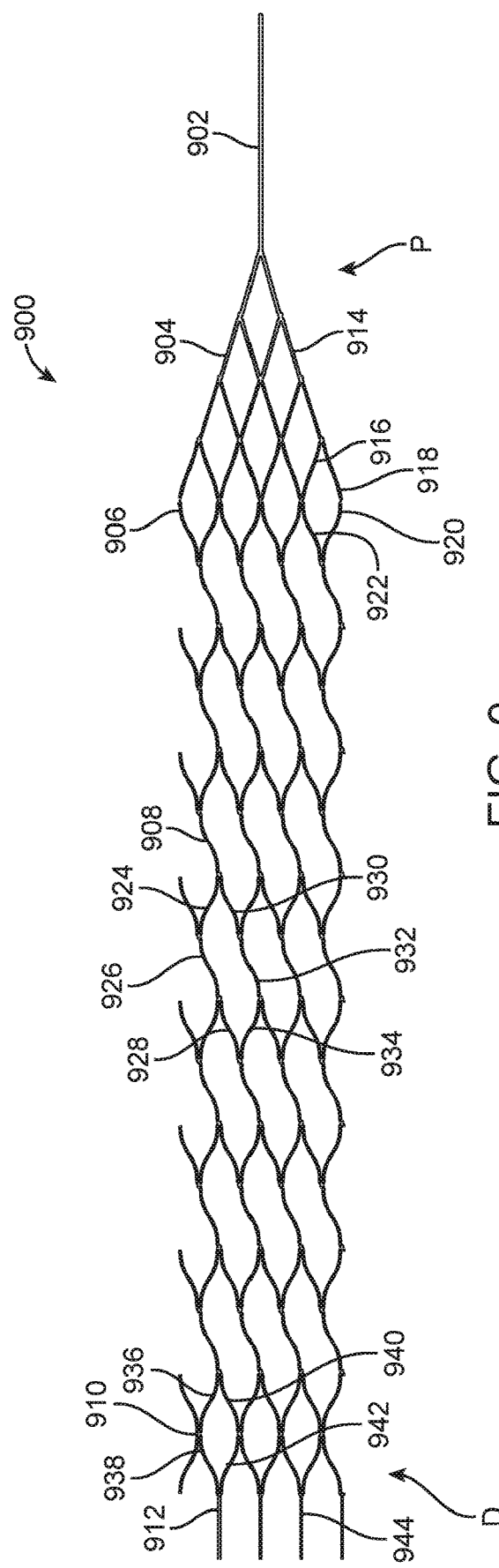
FIG. 9 shows another example of an expandable capture cage in a flat unrolled configuration.

FIG. 9 shows another example of an expandable cage that may be used with any clot retrieval catheters described herein. Here, the clot retrieval catheter only shows the expandable capture cage 900 having a proximal end P and a distal end D. The elongate shaft is not shown in this view, although it is generally the same as any of the other elongate shafts coupled to a capture cage described herein, such as in FIGS. 1, 2, 3B, 4A, 6B, 7, and 8A-8K above.

The example in FIG. 9 is an expandable cage 900 that has been unrolled along its longitudinal axis and flattened out. The expandable cage is self-expanding and may be formed from any shape memory material or superelastic material, such as nitinol. The expandable cage includes several regions along its longitudinal axis. Moving from the proximal end to the distal end, the expandable cage includes a single strut 902, a diamond shaped closed cell region 904, a lemon shaped closed cell region 906, an intermediate region 908 having closed cells with a plurality of convex and concave contours resulting in cells that may look like peanuts or edamame bean pods. The next region has closed lemon shaped cells 910, and the expandable cage terminates in a closed tapered porous tip region 912 formed from linear struts that converge to a point. Each region is coupled to the adjacent region. The entire cage may be laser cut or electrical discharge machined (EDM) from hypo tubing or photoetched from a flat sheet of material and then rolled up with opposing edges welded together.

The single strut 902 has a generally rectangular cross-section (the inner and outer surfaces may be slightly arcuate due to the curvature of the hypo tube from which it is cut), and the lateral sides may be slightly angled) but any cross-section may be used and width and thickness may be modified in order to give the strut the desired mechanical properties. The single strut may be wider/shorter or thicker/thinner than the struts in any of the other regions of the capture cage. The single strut 902 extends proximally and may be releasably or fixedly coupled to the distal end of the elongate shaft (not shown) such as a guidewire. The elongate shaft is then used to advance, retract or otherwise manipulate the expandable cage position as it is being delivered to the treatment site. Additional disclosure about how the single strut may be coupled to the elongate shaft is described below.

The region of closed cell diamond shaped cells 904 includes a plurality of columns of diamond shaped cells that decreases in the proximal direction until the last column has only a single diamond shaped cell. This region of the capture cage helps provide desired mechanical properties to the device so that the capture cage has good pushability and trackability to the contours of the vessel as is it being delivered and deployed or during retraction. The strength of the diamond shaped closed cells also give the capture cage desired strength in this region. In this example, the region includes a column of three diamond shaped cells, followed by a column of two diamond shaped cells, followed by the single diamond shaped cell from the distal to proximal end. A column is in the circumferential direction, transverse to the longitudinal axis of the cage. Each diamond shaped cell includes four linear struts 914 coupled together to form the diamond shaped closed cell. Strut width or thickness can be adjusted as needed in order to provide desired mechanical properties. Thus, struts in diamond shaped closed cell region can be thicker or thinner, or wider or shorter than struts in other regions of the capture cage to prevent buckling of the capture cage as it is unsheathed from the microcatheter or sheath. When the diamond shaped closed cell region is rolled up into a cylindrical shape to form the capture cage, an open proximal end of the cage results and has a beveled shape with the gap between opposing edges of the struts decreasing in the proximal direction. The beveled shape is substantially the same as previously described in the examples above. The tapered beveled shape helps align the proximal end of the cage with the sheath and ensures that the cage can be easily retracted into the sheath (if a sheath is used) without getting caught on the distal edge of the sheath. The angles between adjacent struts on the proximal and distal ends of the diamond cell increase as the expandable cage opens and decrease as the cage closes. The angles between adjacent struts at the top and bottom of the diamond cells decrease as the cage expands and increase as the cage collapses.

The region of lemon shaped closed cells 906 in this example includes a single ring (or column) in the circumferential direction of closed lemon shaped cells. Each lemon shaped cell is formed from four struts which may be shared with adjacent cells. Here, the four struts include two linear struts 916, 918 which are coupled together to form a proximal pointed portion of the lemon shape and a sigmoidally shaped strut 922 (sigmoidal in the distal to proximal direction) and an inverse sigmoidally shaped strut 920 (in the distal to proximal direction). The sigmoidal and inverse sigmoidally shaped struts are coupled to together to form a distal pointed portion of the lemon shape. The opposite ends of the sigmoidal and inverse sigmoidal struts are coupled to the opposite ends of the two linear struts to form the closed lemon shaped cell. Thus, in this example, the proximal end of the sigmoidally shaped strut is coupled to the distal end of the upper linear strut to form a peak in the lemon shaped cell, and the proximal end of the upper linear strut is coupled to the proximal end of the lower linear strut to form the proximal pointed end of the lemon shape. The distal end of the lower linear strut is coupled to the proximal end of the inverse sigmoidally shaped strut to form a valley in the lemon shaped cell, and the distal end of the inverse shaped strut is coupled to the distal end of the sigmoidally shaped strut to form the distal pointed end of the lemon shape. The sigmoidally shaped strut 922 has a distal concave region that faces outward from the closed cell and a proximal concave region that faces inward toward the closed cell. The inverse sigmoidally shaped strut 920 has a distal concave region that faces outward away from the closed cell and also a proximal concave region that faced inward toward the closed cell. The upper linear strut 916 may be replaced with an inverse sigmoidally shaped strut and the lower linear strut 918 may be replaced with a sigmoidally shaped strut such as described in the lemon shaped cells in the examples above or in the lemon shaped cells on the distal end of the cage 900 as will be described below. The linear struts, sigmoidal shaped strut or inverse sigmoidal shaped strut may be wider/shorter or thicker/thinner than the struts in any of the other regions of the capture cage.

The intermediate region 908 of closed cells include a plurality of closed rings extending circumferentially around the longitudinal axis of the expandable cage 900. Each ring includes a plurality of closed cells which are roughly shaped like a peanut or edamame pod. Each closed cell is formed from six struts which include two upper sigmoidal shaped struts, an upper inverse sigmoidal shaped strut, two lower sigmoidal shaped struts and a lower inverse sigmoidal shaped strut, coupled together to form the closed cell. The sigmoidal and inverse sigmoidal shaped struts may be wider/shorter or thicker/thinner than the struts in any of the other regions of the capture cage.

Each lemon shaped closed cell 908 is formed from a first sigmoidal shaped strut 928 (sigmoidal shaped from distal to proximal direction) coupled to a second sigmoidal shaped strut 926 that is coupled to a first inverse sigmoidal shaped strut. The first inverse sigmoidal shaped strut 924 is coupled to a third sigmoidal shaped strut 930 that is coupled to a fourth sigmoidal shaped strut 932 that is then coupled to a second inverse sigmoidal shaped strut 934. The second inverse sigmoidal shaped strut 934 is coupled to the first sigmoidal shaped strut 928. Thus the proximal end of the first sigmoidal shaped strut 928 is coupled to the distal end of the second sigmoidal shaped strut 926 to form a first peak region and the proximal end of the second sigmoidal shaped strut 926 is coupled to the distal end of the first inverse sigmoidal shaped strut 924 to form a second higher peak. The proximal end of the first inverse sigmoidal shaped strut 924 is coupled to the proximal end of the third sigmoidal shaped strut 930 to form a proximal pointed region of the lemon shaped cell, and the distal end of the third sigmoidal shaped strut 930 is coupled to the proximal end of the fourth sigmoidal shaped strut 932 to form a slight first valley. The distal end of the fourth sigmoidal shaped strut 932 is coupled to the proximal end of the second inverse sigmoidal shaped strut 934 to form a second deeper valley and the distal end of the second inverse sigmoidal shaped strut 934 is coupled to the distal end of the first sigmoidal shaped strut 928 to form a distal pointed portion of the lemon shaped cell. The sigmoidal shaped struts 926, 928 on the upper portion of the lemon shaped cell have a distal portion with a concave region that faces outward as well as a proximal portion with a concave region that faces inward. The upper inverse sigmoidal shaped strut 924 has a distal portion with a concave region facing inward and a proximal portion with a concave region facing outward. The two lower sigmoidal shaped struts 930, 932 have a distal portion with a concave region facing inward, and a proximal portion with a concave region outward. The lower inverse sigmoidal shaped strut 934 has a distal region with a concave region facing outward and a proximal portion with a concave region facing inward. Here, the intermediate region includes seven columns or closed rings of edamame shaped closed cells, although this is not limiting and the number of cells may be increased or decreased in order to accommodate longer or shorter treatment regions.

Continuing distally along the capture cage 900, the next region includes a ring or column of lemon shaped cells 910. Here, there is only a single ring of lemon shaped cells although this is not limiting and the number of rings or columns of lemons shaped cells may be increased as needed. Here, the lemon shaped cells are slightly different than the previous lemon shaped cells 906 since cells 910 are formed from an upper sigmoidal shaped strut 938 coupled to an upper inverse sigmoidal shaped strut 936 coupled to a lower sigmoidal shaped strut 940 coupled to a lower inverse sigmoidal shaped strut 942 that is coupled to the upper sigmoidal shaped strut 938. The sigmoidal and inverse sigmoidal shaped struts may be wider/shorter or thicker/thinner than the struts in any of the other regions of the capture cage. Thus, the proximal end of the upper sigmoidal shaped strut 938 is coupled to the distal end of the upper inverse sigmoidal shaped strut 936 to form a peak and the proximal end of the upper inverse sigmoidal shaped strut 936 is coupled to the proximal end of the lower sigmoidal shaped strut 940 to form a pointed proximal end of the lemon. The distal end of the lower sigmoidal shaped strut 940 is coupled to the proximal end of the lower inverse sigmoidal shaped strut 942 to form a valley in the lemon shape, and the distal end of the lower inverse sigmoidal shaped strut 942 is coupled to the distal end of the upper sigmoidal shaped strut 938 to form a distal pointed end of the lemon.

The proximal most region of the expandable capture cage 900 is a closed porous conical or tapered tip 912 formed from a plurality of linear struts 944. FIG. 9 shows the linear struts 944 extending horizontally and parallel with one another because FIG. 9 illustrates the capture cage in a flat unrolled view. The conical or tapered shaped will be more apparent in later figures. Here the closed porous conical or tapered tip 912 is formed from four linear struts 944 that have a proximal end and a distal end. The proximal end of the linear struts 944 is coupled to the distal pointed end of each lemon shaped closed cell and the linear struts extend distally. They extend radially inward to form a tapered or conical tip and the distal ends of the linear struts converge to a point where they are coupled together as will be described in greater detail below. The gap between the linear struts creates a porous tip 912 and the gap is small enough to prevent thrombus from escaping the distal tip but large enough to allow blood flow therethrough to prevent ischemia caused by the clot retrieval device. The linear struts may be wider/shorter or thicker/thinner than the struts in any of the other regions of the capture cage.

Figure 10A:
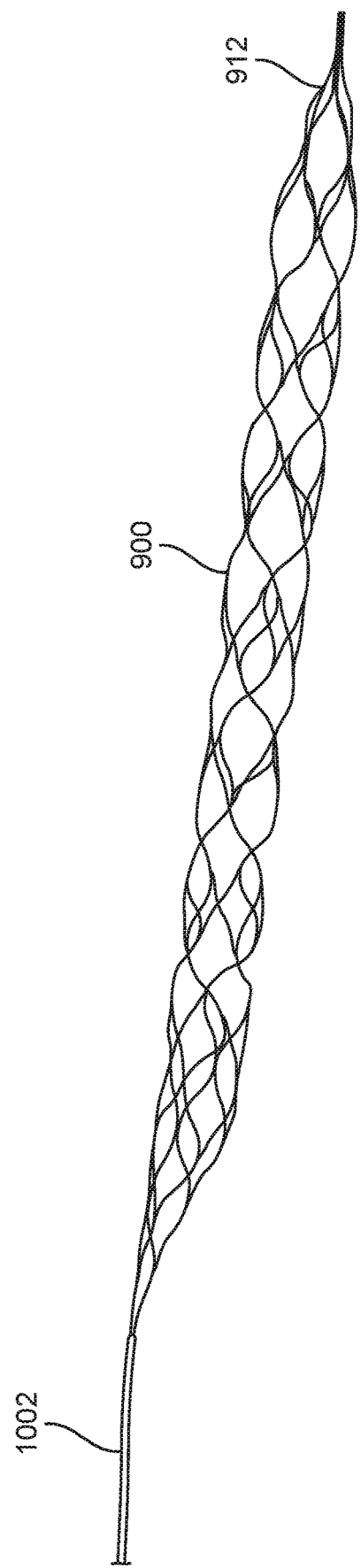
FIG. 10A shows a perspective view of the example in FIG. 9 in the expanded configuration.

FIG. 10A shows the expandable capture cage 900 from FIG. 9 coupled to an elongate shaft 1002 such as a guidewire. The expandable capture cage 900 is in the expanded configuration. Also, the closed tapered or conical distal tip 912 is more clearly visible in this view.

Figure 10B:
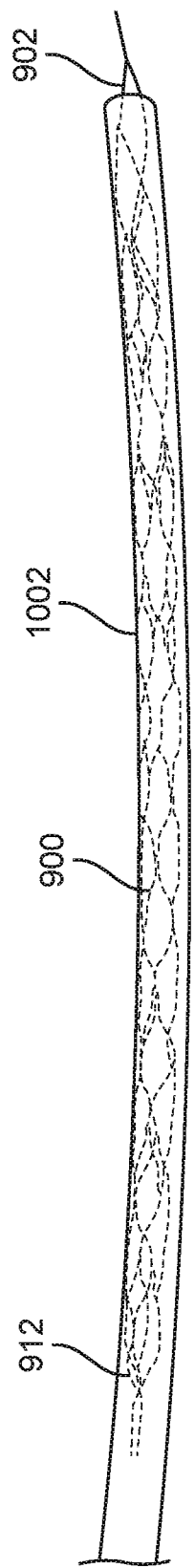
FIG. 10B shows the example of FIG. 9 in a collapsed configuration.

FIG. 10B show the expandable capture cage 900 from FIG. 9 in the collapsed configuration. The conical distal tip 912 helps the capture cage to be slidably advanced into the lumen of an outer sheath 1002 (or the microcatheter or any other tubing) so that the outer sheath constrains the capture cage in the collapsed configuration. The distal end of the conical distal tip 912 is shown with struts extending longitudinally and distally away from the conical distal tip. The radiopaque and/or atraumatic tip formed with a coil may be optionally coupled to the struts. The proximal single strut 902 may be coupled to an elongate shaft such as a guidewire as previously discussed. When the outer sheath 1002 is removed from the capture cage, the capture cage will self-expand into its unbiased expanded configuration.

Figure 11:
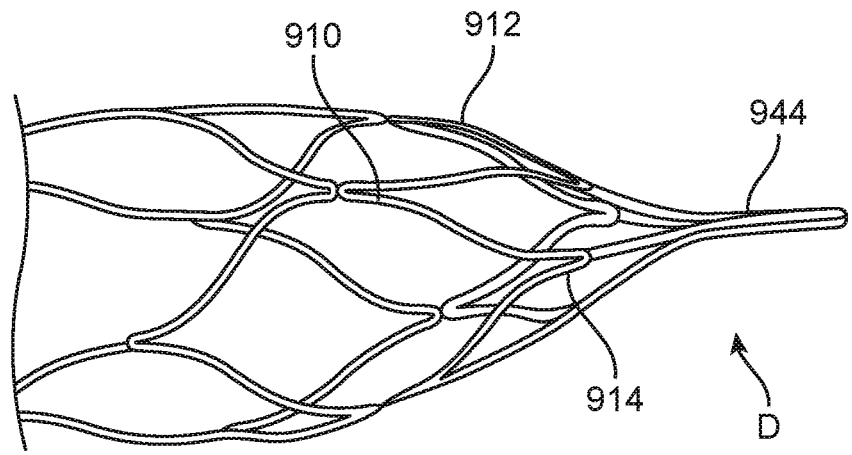
FIG. 11 shows an example of a distal tapered end of a capture cage such as in FIG. 9.

FIG. 11 more clearly illustrates the closed tapered or conical distal porous tip 912 from FIGS. 9-10. Here, the lemon shaped closed cells 910 are visible having a pointed distal end 914 to which the linear struts 944 are coupled. The linear struts 944 extend radially inward toward a centerline of the capture cage and converge to a point distally D, where the distal ends of the linear struts are coupled to one another to form a tip. The gap between the linear struts creates a porosity in the closed tapered distal tip but the porosity is not large enough to permit the clot material to escape from the distal porous tip, yet it is porous enough to allow blood flow therethrough to prevent or avoid ischemia.

Figure 12A:
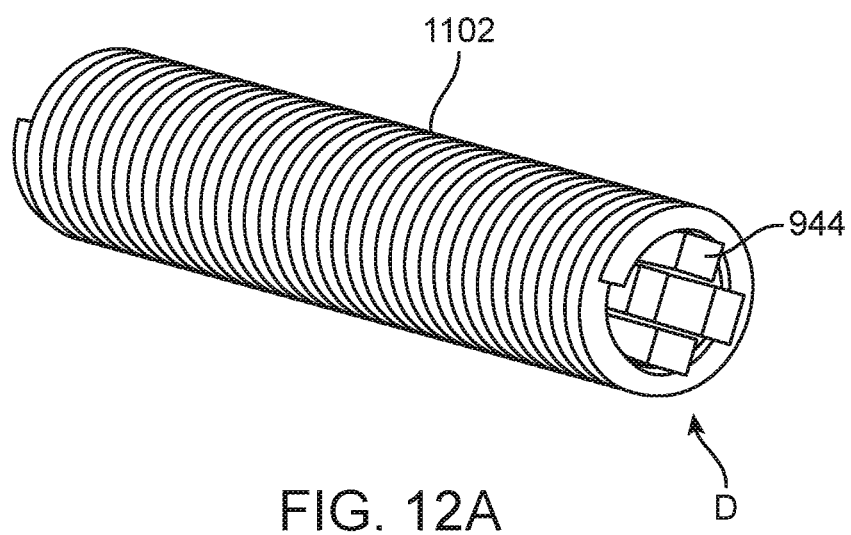
FIGS. 12A-12C show an example of a distal end of a tapered capture cage with a coil tip.

The four linear struts 944 in FIG. 11 converge to a point and this may be sharp. In order to avoid a sharp trauma causing tip, FIG. 12 shows how the distal end of the porous tip may optionally be finished. In FIG. 11, a filament 1102 is helically wrapped around the four linear struts 944 to create an atraumatic tip. The filament may be a metal wire such as stainless steel or nitinol and the filament is helically wound around the four linear struts to prevent them from extending past the helical coil formed by the filament. The filament may then be welded, bonded, soldered, or otherwise coupled to the four linear struts to hold the distal end in a secure configuration. The helical coil therefore forms the atraumatic tip as well as providing a denser portion of the device distally D which enhances radiopacity of the distal tip so that the operator can visualize the position of the device under fluoroscopy or other radiographic imaging. This optional distal tip may be used in any of the examples of clot retrieval devices disclosed herein.

Figure 12B:
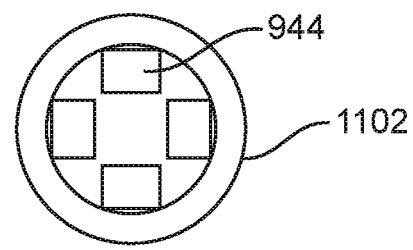

FIG. 12B shows and end view of the distal tip of the tapered or conical distal tip with the four linear struts 944 disposed under the helical coil 1102.

Figure 12C:
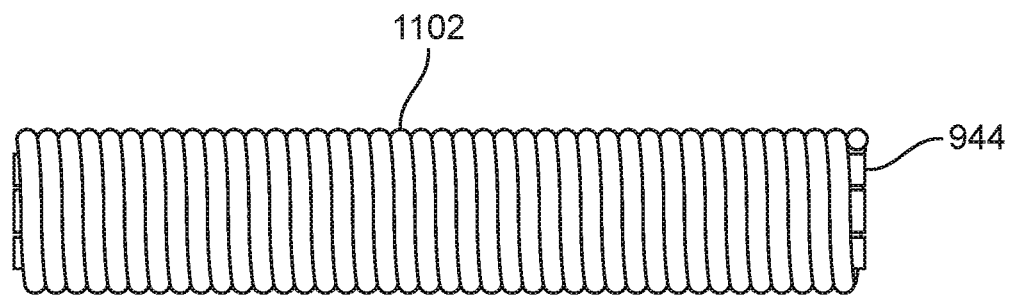

FIG. 12C shows a side view of the distal tip of the tapered or conical distal tip with the four linear struts 944 disposed under the helical coil 1102.

Figure 13A:
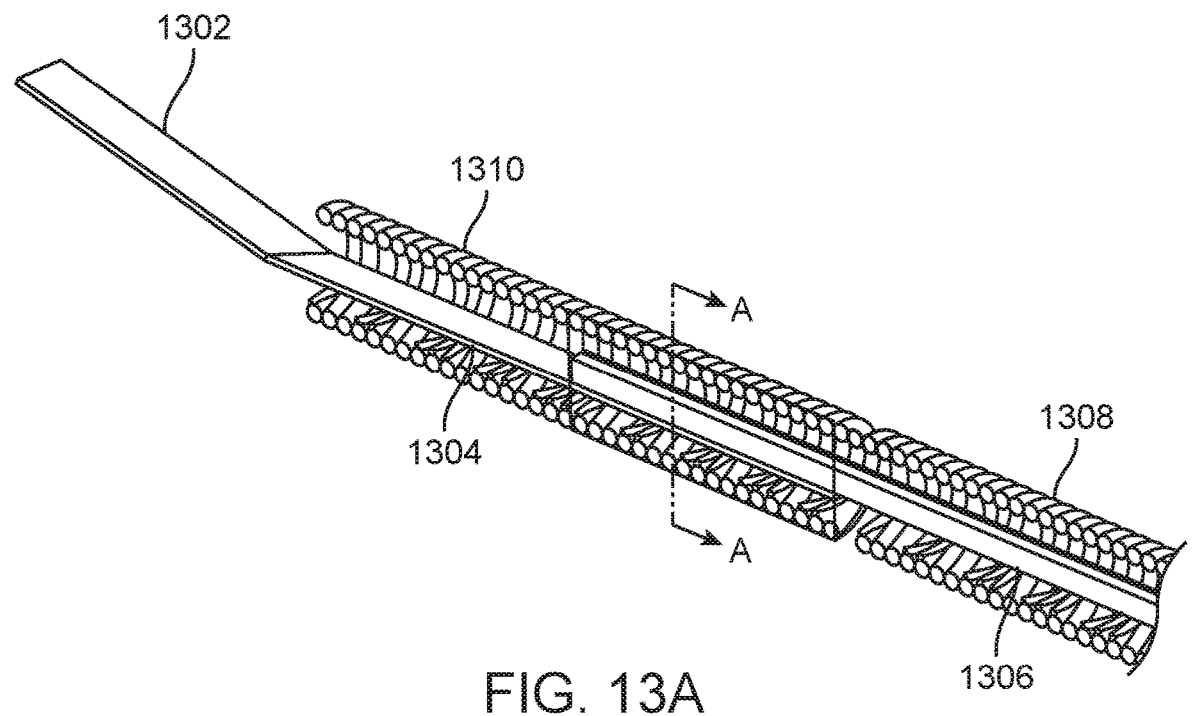
FIGS. 13A-13B show an example of a proximal end of a capture cage coupled to a guidewire.
Figure 13B:
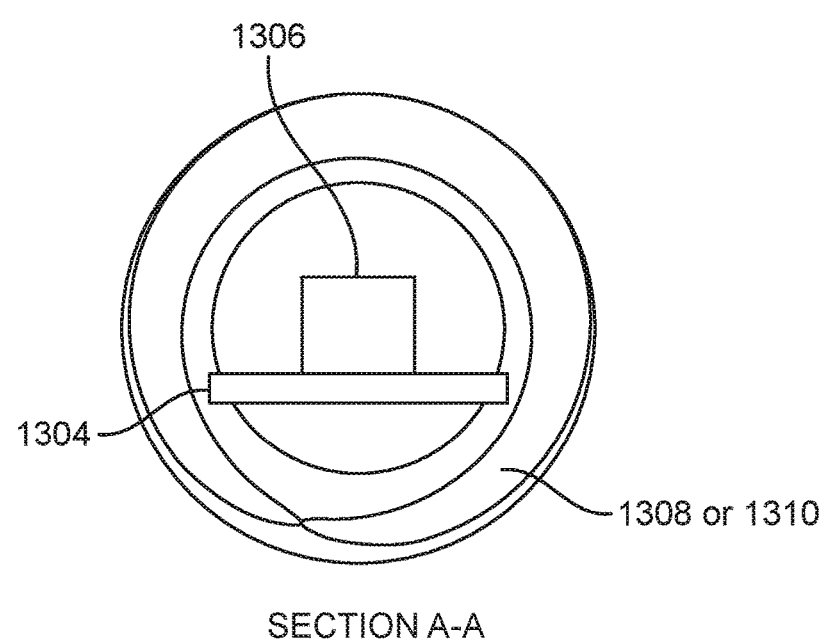

FIGS. 13A-13B show how the proximal end of the capture cage is coupled to the elongate shaft of the clot retrieval catheter.

In FIG. 13A, the single linear strut 1302 which extends proximally from the proximal end of the capture cage may be a flat rectangular wire which tapers down to a more narrow flat rectangular wire 1304 which is disposed under the core wire 1306 of a guidewire coil 1308 when the elongate shaft of the clot retrieval catheter is a guidewire. Here the core wire 1306 may have a square cross-section, although any cross-section may be used. A filament, here a wire such as stainless steel or any other material is helically wrapped around the core wire to form the guidewire coil 1308. The region of overlap between the capture cage single strut 1304 and the guidewire core wire 1306 may be bonded together, welded, soldered or otherwise coupled together thereby securing the capture cage to the elongate shaft, here a guidewire. An additional optional filament 1310 may also be helically wrapped around the proximal end of the single strut 1304 from the capture cage to create a radiopaque marker to help the operator visualize the proximal end of the capture cage under fluoroscopy or other radiographic imaging.

FIG. 13B shows a cross-section of the proximal end of the clot retrieval catheter taken along line A-A in FIG. 13A. Here, the overlapping region between the capture cage single strut 1304 and the guidewire core wire 1306 is clearly visible and this is where the two components may be bonded, welded, or otherwise attached to one another. Also the outer coil which may be either the radiopaque coil 1310 or the guidewire coil 1308 is also seen depending on where the transition between the guidewire coil and the radiopaque coil is. The attachment technique and radiopaque marker feature shown in FIGS. 13A-13B is optional and may be used in any example of a clot retrieval catheter disclosed herein.

Use of the clot retrieval device illustrated in FIGS. 9-13B above is substantially the same as the method of use described in FIGS. 8A-8K above. Retrieval of clots in the neurovascular system are generally related to capture of red clots or white clots. White clots are also known as fibrin rich clots due to the concentration of fibrin in the clot, and red clots are also referred to as RBC rich clots due to the concentration of red blood cells (RBC) in the clot. While the devices in any of the examples described herein may retrieve red clots as effectively or more effectively than commercially available devices, the designs disclosed herein including FIG. 9 appear to capture white clots more effectively than other commercially available clot retrieval devices based on testing. Without being bound by any particular theory, it is believed that the strut geometry permits more effective recovery of white clots compared to red clots. Thus, the struts due to their shape and mechanical properties are more capable of enmeshing the white clots and the capture cage is then able to hold onto the white clots and remove them from the vessel. The strut width and shape may enable this clinical result. The design of FIG. 9 has the shape previously described and the strut width may range from roughly 0.0254 mm to about 0.1016 mm (roughly 0.001 inches to 0.004 inches), or from about 0.0508 mm to about 0.0889 mm (about 0.0020 inches to about 0.0035 inches), and the thickness is determined by the thickness of the hypotube from which the struts are cut. Therefore, strut thickness may range from about 0.0254 mm to about 0.127 mm (about 0.001 inches to about 0.005 inches), or from about 0.0508 mm to about 0.1016 mm (about 0.002 inches to about 0.004 inches), or from about 0.0762 mm to about 0.0889 mm (about 0.003 inches to about 0.0035 inches). In one example, the nominal dimensions are about 0.09144 mm (about 0.0036 inches thick) by 0.0508 mm to about 0.08889 mm (about 0.0020 inches to about 0.0035 inches wide). In the example of FIG. 9, the struts in the clot engaging segment of the expandable cage may have a total strut contact area of about 41.52 square millimeters (about 0.064357 square inches), and thus in the nominal case where the capture cage has a nominal 5 Newton radial force, the force per unit area would be about 5 Newtons per 41.52 square millimeters, or 0.1204 Newtons per square millimeter. This calculation may be repeated for the other ranges of radial force disclosed herein.

Also, the capture cage design has a radial force (the ability to resist collapse) of about 1 to 10 Newtons, or about 1 to 8 Newtons, or about 1 to about 6 Newtons or about 1 to 5 Newtons. In one example the nominal radial force is about 5 Newtons. The capture cage may have any number of struts extending circumferentially around the device, for example in the example of FIG. 9, the cage has 4 to 8 struts extending circumferentially around the capture cage depending on the longitudinal location, therefore the radial force per strut ranges from about 1 Newton per 8 struts, or 0.125 Newtons per strut radial strength to about 1 Newton per 4 struts, or 0.25 Newtons per strut radial strength on the low end of the range, to the high end of the scale of about 10 Newtons per 8 struts, or about 1.25 Newtons per strut radial strength to about 10 Newtons per 4 struts, or about 2.5 Newtons per strut radial strength. When the nominal radial strength is 5 Newtons, then radial strength per strut ranges from about 5 Newtons per 8 struts, or 0.625 Newtons per strut radial strength to about 5 Newtons per 4 struts, or 1.25 Newtons per strut radial strength. Other radial strengths per number of struts may also be calculated using any of the ranges of radial strength normalized with the any of the ranges of struts disclosed herein. These radial strengths per strut may be a factor in ensuring capture and removal of red and white clots as effectively or more effectively than commercially available devices. But, given the cell geometry and mechanical properties of the device including radial strength per strut, the examples disclosed herein, including FIG. 9 appear to be more effective at removing tough to remove clots (such as white clots) when compared to commercially available devices.

Optionally, any example of a clot retrieval device disclosed herein may also be used to deliver a therapeutic agent to the treatment site. For example, a thrombolytic drug such as streptokinase or urokinase may also be delivered by the device. Other therapeutic drugs such as blood thinners like heparin may also be delivered to the treatment site by the clot retriever.

NOTES AND EXAMPLES

The following, non-limiting examples, detail certain aspects of the present subject matter to solve the challenges and provide the benefits discussed herein, among others.

Example 1 is a device for removing an obstruction from a blood vessel, the device comprising: an elongate flexible shaft having a proximal end and a distal end; an expandable capture cage having a proximal end and a distal end, wherein the proximal end of the capture cage is coupled to the distal end of the elongate shaft, wherein the expandable capture cage has a collapsed configuration and an expanded configuration, wherein in the collapsed configuration the expandable capture cage is adapted to be delivered through the vessel, and wherein in the expanded configuration the expandable capture cage is configured to expand into and enmesh the obstruction so that the obstruction may be removed from the blood vessel by proximal retraction of the expandable capture cage.

Example 2 is the device of Example 1, wherein the obstruction is a thrombus.

Example 3 is the device of any of Examples 1-2, wherein the thrombus comprises a white clot or a red clot.

Example 4 is the device of any of Examples 1-3, wherein the elongate flexible shaft is a guidewire.

Example 5 is the device of any of Examples 1-4, wherein the expandable cage is self-expanding.

Example 6 is the device of any of Examples 1-5, wherein the proximal end of the expandable capture cage is open and comprises a proximal edge that is beveled relative to a longitudinal axis of the expandable capture cage.

Example 7 is the device of any of Examples 1-6, wherein the proximal end of the expandable capture cage comprises a plurality of open or closed rings, each open or closed ring in the plurality of open or closed rings comprising one or more closed cells, and wherein each open or closed ring has a total number of closed cells, wherein the total number of closed cells decreases in the proximal direction until a proximal-most ring is an open ring having a single closed cell.

Example 8 is the device of any of Examples 1-7, wherein the proximal end of the expandable capture cage comprises a plurality of rings, and wherein at least some of the plurality of rings are open rings with a gap disposed between opposite edges of the open rings, and wherein the gap increases in a proximal direction.

Example 9 is the device of any of Examples 1-8, wherein the expandable cage comprises a plurality of struts coupled together, and wherein at least some of the plurality of struts disposed on the proximal end of the expandable cage have a width or thickness less than that of some of the plurality of struts disposed distal thereof.

Example 10 is the device of any of Examples 1-9, wherein the expandable cage tapers from the proximal end of the expandable cage toward the distal end of the expandable cage.

Example 11 is the device of any of Examples 1-10, wherein the expandable cage comprises a plurality of closed cells, the plurality of closed cells having a lemon shape.

Example 12 is the device of any of Examples 1-11, wherein the closed cells comprise a tapering proximal end, a tapering distal end, a peak between the tapering proximal and distal end, and a valley between the tapering proximal and distal end.

Example 13 is the device of any of Examples 1-12, wherein the expandable cage comprises a plurality of closed cells, the plurality of closed cells comprising a plurality of concave and a plurality of convex contours.

Example 14 is the device of any of Examples 1-13, wherein some of the plurality of closed cells comprise six sigmoidally shaped or inverse sigmoidally shaped struts, wherein a first sigmoidally shaped strut has a distal end with a concave region facing outward and a proximal end with a concave region facing inward, wherein a second sigmoidally shaped strut has a distal end with a concave region facing outward and a proximal end with concave region facing inward, wherein a third inverse sigmoidally shaped strut has a proximal end with a concave region facing outward and a distal end with a concave region facing inward, wherein a fourth sigmoidally shaped strut has a proximal end with a concave region facing outward and a distal end with a concave region facing inward, wherein a fifth sigmoidally shaped strut has a proximal end with a concave region facing outward and a distal end with a concave region facing inward, and wherein a sixth inverse sigmoidally shaped strut has a proximal end with a concave region facing inward and a distal end with a concave region facing outward.

Example 15 is the device of any of Examples 1-14, wherein the proximal end of the first sigmoidally shaped strut is coupled to the distal end of the second sigmoidally shaped strut, wherein the proximal end of the second sigmoidally shaped strut is coupled to the distal end of the third inverse sigmoidally shaped strut, wherein the proximal end of the third inverse sigmoidally shaped strut is coupled to proximal end of the fourth sigmoidally shaped strut, wherein the distal end of the forth sigmoidally shaped strut is coupled to proximal end of the fifth sigmoidally shaped strut, wherein the distal end of the fifth sigmoidally shaped strut is coupled to the proximal end of the sixth inverse sigmoidally shaped strut, wherein the distal end of the sixth inverse sigmoidally shaped strut is coupled to distal end of the first sigmoidally shaped strut.

Example 16 is the device of any of Examples 1-15, wherein the proximal end of the expandable cage comprises a plurality lemon shaped cells and a plurality of diamond shaped cells.

Example 17 is the device of any of Examples 1-16, wherein the plurality of lemon shaped cells comprise a sigmoidally shaped strut, a first linear strut, a second linear strut, and an inverse sigmoidally shaped strut, wherein the sigmoidally shaped strut is coupled to the first linear strut, the first linear strut coupled to the second linear strut, the second linear strut coupled to the inverse sigmoidally shaped strut, and wherein the inverse sigmoidally shaped strut is coupled to the sigmoidally shaped strut.

Example 18 is the device of any of Examples 1-17, wherein the plurality of diamond shaped cells comprise four linear struts coupled together.

Example 19 is the device of any of Examples 1-18, wherein the proximal end of the expandable cage comprises a decreasing number of diamond shaped cells, wherein a last diamond shaped cell in the deceasing number of diamond shaped cells is coupled with the elongate shaft.

Example 20 is the device of any of Examples 1-19, wherein the proximal end of the expandable capture cage terminates in a single strut overlapping with and coupled to the distal end of the elongate shaft.

Example 21 is the device of any of Examples 1-20, further comprising a filament helically disposed around the single strut and the elongate shaft to form a flexible radiopaque joint.

Example 22 is the device of any of Examples 1-21, wherein the distal end of the expandable cage is comprises a plurality of lemon shaped closed cells, each lemon shaped closed cell having a pointed distal region.

Example 23 is the device of any of Examples 1-22, wherein the lemon shaped closed cells comprise four sigmoidally or inverse sigmoidally shaped struts, wherein a first sigmoidally shaped strut has a distal end with a concave region facing outward and a proximal end with a concave region facing inward, wherein a second inverse sigmoidally shaped strut has a distal end with a concave region facing inward and a proximal end with a concave region facing outward, wherein a third sigmoidally shaped strut has a proximal end with a concave region facing outward and a distal end with a concave region facing inward, wherein the fourth inverse sigmoidally shaped strut has a proximal end with a concave region facing inward and a distal end with a concave region facing outward.

Example 24 is the device of any of Examples 1-23, wherein the proximal end of the first sigmoidally shaped strut is coupled to the distal end of the second inverse sigmoidally shaped strut to form a peak in the lemon shaped closed cell, wherein the proximal end of the second inverse sigmoidally shaped strut is coupled to the proximal end of the third sigmoidally shaped strut to form a pointed proximal end of the lemon shaped closed cell, wherein the distal end of the third sigmoidally shaped strut is coupled to the proximal end of the fourth inverse sigmoidally shaped strut to form a valley in the lemon shaped closed cell, and wherein the distal end of the fourth inverse sigmoidally shaped strut is coupled to the distal end of the first sigmoidally shaped strut to form a pointed distal end of the lemon shaped closed cell.

Example 25 is the device of any of Examples 1-24, wherein the peak of the closed cell is concave facing inward and the valley of the closed cell is concave facing inward.

Example 26 is the device of any of Examples 1-25, wherein the distal end of the expandable capture cage comprises a plurality of linear struts coupled to the pointed distal region of the plurality of lemon shaped cells, the linear struts tapering distally to a point to form a closed porous tip configured to prevent the obstruction from passing therethrough.

Example 27 is the device of any of Examples 1-26, further comprising a helically coiled filament disposed around the linear struts to form an atraumatic radiopaque tip.

Example 28 is a system for removing an obstruction from a blood vessel, the system comprising the device of any of Examples 1-27; and a microcatheter slidably disposed over the device.

Example 29 is the system of Example 28, further comprising a sheath slidably disposed over the microcatheter.

Example 30 is a method for removing an obstruction from a vessel, said method comprising: providing a clot retrieving catheter comprising an expandable capture cage coupled to an elongate flexible shaft; introducing the clot retrieving catheter into the vessel; advancing the expandable capture cage through the vessel to the obstruction; radially expanding the expandable capture cage into engagement with the obstruction; enmeshing the obstruction with the expandable capture cage; removing the obstruction from the vessel with the clot retrieving catheter; and removing the clot retrieving catheter from the vessel.

Example 31 is the method of Example 30, wherein advancing the expandable capture cage through the vessel comprise advancing the elongate flexible shaft through a microcatheter.

Example 32 is the method of any of Examples 30-31, wherein advancing the expandable capture cage comprises advancing the expandable capture cage distal of the obstruction or advancing the microcatheter distal of the obstruction.

Example 33 is the method of any of Examples 30-32, further comprising advancing the microcatheter over a guidewire, and removing the guidewire from the patient before introducing the clot retrieving catheter into the vessel.

Example 34 is the method of any of Examples 30-33, wherein the obstruction comprises a thrombus.

Example 35 is the method of any of Examples 30-34, wherein the thrombus comprises a white clot or a red clot.

Example 36 is the method of any of Examples 30-35, wherein the vessel is an arterial vessel in a head of a patient.

Example 37 is the method of any of Examples 30-36, wherein radially expanding the expandable capture cage comprises proximally retracting a microcatheter away from the expandable capture cage to remove a constraint therefrom.

Example 38 is the method of any of Examples 30-37, wherein radially expanding the expandable capture cage comprises causing the expandable capture cage to self-expand.

Example 39 is the method of any of Examples 30-38, wherein radially expanding the expandable capture cage comprises expanding a plurality of closed cells formed with a plurality of sigmoidally shaped and inverse sigmoidally shaped struts coupled together.

Example 40 is the method of any of Examples 30-39, further comprising preventing the obstruction from exiting a distal end of the expandable capture cage with a tapered tip coupled thereto.

Example 41 is the method of any of Examples 30-40, wherein removing the obstruction from the vessel comprises proximally retracting the expandable capture cage.

Example 42 is the method of any of Examples 30-41, wherein proximally retracting the expandable capture cage comprises retracting a beveled proximal edge of the expandable capture cage toward a distal end of a microcatheter or a sheath.

Example 43 is the method of any of Examples 30-42, further comprising visualizing radiopaque markers on the expandable capture cage with fluoroscopy.

Example 44 is a device for removing an obstruction from a vessel, comprising: an elongate flexible shaft having a proximal end and a distal end; an expandable capture cage having a proximal end and a distal end, wherein the proximal end of the capture cage is coupled to the distal end of the elongate shaft, wherein the expandable capture cage has a collapsed configuration and an expanded configuration, wherein in the collapsed configuration the expandable capture cage is adapted to be delivered through the vessel, and wherein in the expanded configuration the expandable capture cage is configured to expand into and enmesh the obstruction.

Example 45 is the device of Example 44, wherein the expandable cage is formed from a nickel-titanium alloy.

Example 46 is the device of any of Examples 44-45, wherein the distal end of the expandable capture cage is closed and comprises a distally tapering porous tip.

Example 47 is the device of any of Examples 44-46, wherein the distally tapering tip comprises a plurality of linear struts or arcuate struts extending from the distal end of the expandable cage and converging to a point.

Example 48 is the device of any of Examples 44-47, wherein the expandable cage comprises a plurality of interconnected struts, and wherein at least some of the plurality of linear struts or arcuate struts in the tapering tip are thinner than at least some of the plurality of interconnected struts in the expandable cage.

Example 49 is the device of any of Examples 44-48, wherein the expandable cage comprises a plurality of closed cells having peaks, valleys and pointed regions, and wherein the plurality of linear struts or arcuate struts are coupled either one of the peaks, one of the valleys, one of the pointed regions, or an area disposed between one of the peaks or valleys and one of the pointed regions.

Example 50 is the device of any of Examples 44-49, wherein the plurality of linear struts comprise struts having a first length and struts having a second length longer than first length, and wherein the struts with the first length are coupled to the pointed region and the struts of the second length are coupled to a peak or a valley, thereby permitting the distal tapering tip to accommodate for foreshortening of the expandable cage.

Example 51 is the device of any of Examples 44-50, wherein the proximal end of the expandable capture cage comprises a plurality of struts converging proximally into a linear strut that is coupled to the distal end of the elongate flexible shaft.

Example 52 is the device of any of Examples 44-51, wherein the proximal end of the expandable capture cage comprises a plurality of rings, each ring in the plurality of rings comprising one or more closed cells, and wherein each ring has a total number of closed cells, wherein the total number of closed cells decreases in the proximal direction until a proximal-most ring is an open ring having a single closed cell.

Example 53 is the device of any of Examples 44-52, further comprising a proximal radiopaque marker disposed adjacent the proximal end of the expandable cage, or a distal radiopaque marker disposed adjacent the distal end of the expandable cage.

Example 54 is the device of any of Examples 44-53, wherein the expandable cage comprises a plurality of closed cells, wherein at least some of the plurality of closed cells are coupled together while at least some of the plurality of closed cells are disconnected from an adjacent closed cell, thereby forming a gap which creates a flexible region in the expandable cage.

Example 55 is the device of any of Examples 44-54, wherein the expandable cage comprises a plurality of struts coupled together, and wherein the expandable cage comprises one or more regions with two or more side-by-side struts running parallel with one another.

Example 56 is the device of any of Examples 44-55, wherein the expandable cage comprises a plurality of struts coupled together, further comprising one or more radiopaque markers coupled to one or more of the plurality of struts.

Example 57 is the device of any of Examples 44-56, further comprising an outer sheath or a microcatheter disposed over the expandable cage, the outer sheath or microcatheter constraining the expandable cage and holding it in the collapsed configuration.

Example 58 is the device of any of Examples 44-57, wherein a proximal end of at least some of the plurality of closed cells comprises a strut that is thicker than adjacent struts in the at least some of the plurality of closed cells.

Example 59 is the device of any of Examples 44-58, wherein some of the plurality of closed cells comprise four sigmoidally or inverse sigmoidally shaped struts, wherein a first sigmoidally shaped strut has a proximal end with a concave region facing outward and a distal end with a concave region facing inward, wherein a second inverse sigmoidally shaped strut has a proximal end with a concave region facing inward and a distal end with a concave region facing outward, wherein a third sigmoidally shaped strut has a distal end with a concave region facing outward and a proximal end with a concave region facing inward, wherein the fourth inverse sigmoidally shaped strut has a distal end with a concave region facing inward and a proximal end with a concave region facing outward.

Example 60 is the device of any of Examples 44-59, wherein the distal end of the first sigmoidally shaped strut is coupled to the proximal end of the second inverse sigmoidally shaped strut to form a peak in the closed cell, wherein the distal end of the second inverse sigmoidally shaped strut is coupled to the distal end of the third sigmoidally shaped strut to form a pointed distal end of the closed cell, wherein the proximal end of the third sigmoidally shaped strut is coupled to the distal end of the fourth inverse sigmoidally shaped strut to form a valley in the closed cell, and wherein the proximal end of the fourth inverse sigmoidally shaped strut is coupled to the proximal end of the first sigmoidally shaped strut to form a pointed proximal end of the closed cell.

Example 61 is the device of any of Examples 44-60, wherein the peak of the closed cell is concave facing inward and the valley of the closed cell is concave facing inward.

Example 62 is a system for removing an obstruction from a vessel, said system comprising a clot retrieving catheter comprising an expandable capture cage coupled to an elongate flexible, wherein the expandable capture cage has a collapsed configuration and an expanded configuration, wherein in the collapsed configuration the expandable capture cage is adapted to be delivered through the vessel, and wherein in the expanded configuration the expandable capture cage is configured to expand into and enmesh the obstruction; and a microcatheter having a lumen sized to slidably receive the clot retrieving catheter.

Example 63 is the system of Example 62, further comprising a sheath slidably disposed over the expandable capture cage.

In Example 64, the apparatuses, systems or methods of any one or any combination of Examples 1-63 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A device for removing an obstruction from a blood vessel, the device comprising:
   an elongate flexible shaft having a proximal end and a distal end;
   an expandable capture cage having a proximal end and a distal end, wherein the proximal end of the capture cage is coupled to the distal end of the elongate shaft,
   wherein the expandable cage comprises a plurality of closed cells, the plurality of closed cells comprises a plurality of concave contours and a plurality of convex contours,
   wherein some of the plurality of closed cells each comprise six struts, the six struts being sigmoidally shaped struts or inverse sigmoidally shaped struts,
   wherein a first strut is sigmoidally shaped and has a distal end with a concave region facing outward and a proximal end with a concave region facing inward,
   wherein a second strut is sigmoidally shaped and has a distal end with a concave region facing outward and a proximal end with concave region facing inward,
   wherein a third strut is inverse sigmoidally shaped and has a proximal end with a concave region facing outward and a distal end with a concave region facing inward,
   wherein a fourth strut is sigmoidally shaped and has a proximal end with a concave region facing outward and a distal end with a concave region facing inward,
   wherein a fifth strut is sigmoidally shaped and has a proximal end with a concave region facing outward and a distal end with a concave region facing inward, and
   wherein a sixth strut is inverse sigmoidally shaped and has a proximal end with a concave region facing inward and a distal end with a concave region facing outward,
   wherein the expandable capture cage has a collapsed configuration and an expanded configuration,
   wherein in the collapsed configuration the expandable capture cage is adapted to be delivered through the vessel, and
wherein in the expanded configuration the expandable capture cage is configured to expand into and enmesh the obstruction so that the obstruction may be removed from the blood vessel by proximal retraction of the expandable capture cage.

2. The device of claim 1, wherein the obstruction is a thrombus.

3. The device of claim 2, wherein the thrombus comprises a white clot or a red clot.

4. The device of claim 1, wherein the elongate flexible shaft is a guidewire.

5. The device of claim 1, wherein the expandable cage is self-expanding.

6. The device of claim 1, wherein the proximal end of the expandable capture cage is open and comprises a proximal edge that is beveled relative to a longitudinal axis of the expandable capture cage.

7. The device of claim 1, wherein the proximal end of the expandable capture cage comprises a plurality of open or closed rings, each open or closed ring in the plurality of open or closed rings comprising one or more closed cells, and wherein each open or closed ring has a total number of closed cells, wherein the total number of closed cells in an open or closed ring is less than the total number of closed cells in an adjacent open ring distal thereof or an adjacent closed ring distal thereof until a proximal-most ring is an open ring having a single closed cell.

8. The device of claim 1, wherein the proximal end of the expandable capture cage comprises a plurality of rings, and wherein at least some of the plurality of rings are open rings with a gap disposed between opposite edges of the open rings, and wherein the gap increases in a proximal direction.

9. The device of claim 1, wherein the expandable cage comprises a plurality of struts coupled together, and wherein at least some of the plurality of struts disposed on the proximal end of the expandable cage have a width or thickness less than that of some of the plurality of struts disposed distal thereof.

10. The device of claim 1, wherein the expandable cage tapers from the proximal end of the expandable cage toward the distal end of the expandable cage.

11. The device of claim 1, wherein some of the plurality of closed cells comprise a tapering proximal end, a tapering distal end, a peak between the tapering proximal and distal ends, and a valley between the tapering proximal and distal ends.

12. The device of claim 1, wherein the proximal end of the first strut is coupled to the distal end of the second strut,
   wherein the proximal end of the second strut is coupled to the distal end of the third strut,
   wherein the proximal end of the third strut is coupled to the proximal end of the fourth strut, wherein the distal end of the fourth sigmoidally shaped strut is coupled to the proximal end of the fifth sigmoidally shaped strut,
   wherein the distal end of the fifth strut is coupled to the proximal end of the sixth strut, and
   wherein the distal end of the sixth strut is coupled to the distal end of the first strut.

13. The device of claim 1, wherein the proximal end of the expandable cage comprises some of the plurality of closed cells, which comprise a plurality of diamond shaped cells and a plurality of closed cells, each of the plurality of closed cells comprising at least one proximal sigmoidally shaped struts and at least one proximal inverse sigmoidally shaped struts coupled together.

14. The device of claim 13, wherein the at least one of the proximal sigmoidally shaped struts and the at least one of proximal inverse sigmoidally shaped struts comprise a sigmoidally shaped proximal strut and an inverse sigmoidally shaped proximal strut, the device further comprising a first linear strut and a second linear strut, wherein the sigmoidally shaped proximal strut is coupled to the first linear strut, the first linear strut is coupled to the second linear strut, the second linear strut is coupled to the inverse sigmoidally shaped proximal strut, and wherein the inverse sigmoidally shaped proximal strut is coupled to the sigmoidally shaped proximal strut.

15. The device of claim 13, wherein the plurality of diamond shaped cells comprise four linear struts coupled together.

16. The device of claim 13, wherein the proximal end of the expandable cage comprises a plurality of circumferential rings each having a total number of diamond shaped cells, wherein the total number of diamond shaped cells in one circumferential ring is less than the total number of diamond shaped cells in an adjacent circumferential ring distal thereof, and wherein a last diamond shaped cell in the the plurality of circumferential rings having a total number of diamond shaped cells is coupled with the elongate shaft.

17. The device of claim 1, wherein the proximal end of the expandable capture cage terminates in a single strut overlapping with and coupled to the distal end of the elongate shaft.

18. The device of claim 17, further comprising a filament helically disposed around the single strut and the elongate shaft to form a flexible radiopaque joint.

19. The device of claim 1, wherein the distal end of the expandable cage comprises some of the plurality of closed cells, the plurality of closed cells each comprising a plurality of sigmoidally shaped struts and a plurality of inverse sigmoidally shaped struts coupled together to form a pointed distal region.

20. The device of claim 19, wherein the the plurality of closed cells in the distal end of the expandable cage each comprise four distal struts,
wherein a first distal strut is sigmoidally shaped and has a distal end with a concave region facing outward and a proximal end with a concave region facing inward,
wherein a second distal strut is inverse sigmoidally shaped and has a distal end with a concave region facing inward and a proximal end with a concave region facing outward,
wherein a third distal strut is sigmoidally shaped and has a proximal end with a concave region facing outward and a distal end with a concave region facing inward, and
wherein a fourth distal struts is inverse sigmoidally shaped and has a proximal end with a concave region facing inward and a distal end with a concave region facing outward.

21. The device of claim 20, wherein the proximal end of the first distal strut is coupled to the distal end of the second distal strut to form a peak in the plurality of closed cells in the distal end of the expandable cage,
wherein the proximal end of the second distal strut is coupled to the proximal end of the third distal strut to form a pointed proximal end in the plurality of closed cells in the distal end of the expandable cage,
wherein the distal end of the third distal strut is coupled to the proximal end of the fourth distal strut to form a valley in the plurality of closed cells in the distal end of the expandable cage, and
wherein the distal end of the fourth distal strut is coupled to the distal end of the first distal strut to form a pointed distal end in the plurality of closed cells in the distal end of the expandable cage.

22. The device of claim 21, wherein the peak is concave facing inward and the valley is concave facing inward.

23. The device of claim 19, wherein the distal end of the expandable capture cage comprises a plurality of linear struts coupled to the pointed distal region, the linear struts tapering distally to a point to form a closed porous tip configured to prevent the obstruction from passing therethrough.

24. The device of claim 23, further comprising a helically coiled filament disposed around the linear struts to form an atraumatic radiopaque tip.

25. A system for removing an obstruction from a blood vessel, the system comprising:
the device of claim 1; and
a microcatheter slidably disposed over the device.

26. The system of claim 25, further comprising a sheath slidably disposed over the microcatheter.

27. A device for removing an obstruction from a blood vessel, the device comprising:
an elongate flexible shaft having a proximal end and a distal end;
an expandable capture cage having a proximal end and a distal end, wherein the proximal end of the capture cage is coupled to the distal end of the elongate shaft,
wherein the expandable capture cage comprises a plurality of closed cells, some of the plurality of closed cells comprising a plurality of concave contours and a plurality of convex contours,
wherein the proximal end of the expandable capture cage comprises a plurality of sigmoidally shaped struts and a plurality of inverse sigmoidally shaped struts coupled together to form some of the plurality of closed cells and a plurality of diamond shaped cells,
wherein the expandable capture cage has a collapsed configuration and an expanded configuration,
wherein in the collapsed configuration the expandable capture cage is adapted to be delivered through the vessel, and
wherein in the expanded configuration the expandable capture cage is configured to expand into and enmesh the obstruction so that the obstruction may be removed from the blood vessel by proximal retraction of the expandable capture cage.

28. The device of claim 27, wherein the obstruction is a thrombus.

29. The device of claim 27, wherein the elongate flexible shaft is a guidewire.

30. The device of claim 27, wherein the expandable cage is self-expanding.

31. The device of claim 27, wherein the proximal end of the expandable capture cage is open and comprises a proximal edge that is beveled relative to a longitudinal axis of the expandable capture cage.

32. The device of claim 27, wherein the proximal end of the expandable capture cage comprises a plurality of open or closed rings, each open or closed ring in the plurality of open or closed rings comprising one or more closed cells, and wherein each open or closed ring has a total number of closed cells, wherein the total number of closed cells in an open or closed ring is less than the total number of closed cells in an adjacent open ring distal thereof or an adjacent closed ring distal thereof until a proximal-most ring is an open ring having a single closed cell.

33. The device of claim 27, wherein the proximal end of the expandable capture cage comprises a plurality of rings, and wherein at least some of the plurality of rings are open rings with a gap disposed between opposite edges of the open rings, and wherein the gap increases in a proximal direction.

34. The device of claim 27, wherein the expandable cage tapers from the proximal end of the expandable cage toward the distal end of the expandable cage.

35. The device of claim 27, wherein some of the plurality of closed cells comprise a plurality of sigmoidally shaped struts and a plurality of inverse sigmoidally shaped struts coupled together.

36. The device of claim 27, wherein the proximal end of the expandable capture cage terminates in a single strut overlapping with and coupled to the distal end of the elongate shaft.

37. A system for removing an obstruction from a blood vessel, the system comprising:
the device of claim 27; and
a microcatheter slidably disposed over the device.

* * * * *

UNITED STATES PATENT AND TRADEMARK OFFICE
CERTIFICATE OF CORRECTION

PATENT NO. : 11,291,463 B2
APPLICATION NO. : 17/336791
DATED : April 5, 2022
INVENTOR(S) : Atchaneeyasakul et al.

It is certified that error appears in the above-identified patent and that said Letters Patent is hereby corrected as shown below:

In the Specification

In Column 2, Line 64, delete "116." and insert --110.-- therefor

In Column 2, Line 66, after "proximal portion", delete "110"

In Column 7, Line 42, after "cross-section,", delete "section,"

In Column 11, Line 33, delete "micro catheter" and insert --microcatheter-- therefor In Column 13, Line 41, delete "914" and insert --944-- therefor In the Claims In Column 26, Line 35, in Claim 12, after "strut,", insert a linebreak In Column 26, Line 36, in Claim 12, after "fourth", delete "sigmoidally shaped"

In Column 26, Line 37, in Claim 12, after "fifth", delete "sigmoidally shaped"

In Column 26, Line 47, in Claim 13, delete "struts" and insert --strut-- therefor In Column 26, Line 48, in Claim 13, delete "struts" and insert --strut-- therefor In Column 26, Line 49, in Claim 14, after "one", delete "of the"

In Column 26, Line 50, in Claim 14, delete "struts" and insert --strut-- therefor In Column 26, Line 50, in Claim 14, after "one", delete "of"

Signed and Sealed this
Fourth Day of October, 2022

Katherine Kelly Vidal
*Director of the United States Patent and Trademark Office*

CERTIFICATE OF CORRECTION (continued)
U.S. Pat. No. 11,291,463 B2

In Column 26, Line 51, in Claim 14, delete "struts" and insert --strut-- therefor In Column 26, Line 52, in Claim 14, after "strut", insert --,--

In Column 27, Line 3, in Claim 16, delete "the the" and insert --the-- therefor

In Column 27, Line 19, in Claim 20, delete "the the" and insert --the-- therefor In Column 27, Line 33, in Claim 20, delete "struts" and insert --strut-- therefor